(12) United States Patent
Yu

(10) Patent No.: US 11,295,858 B2
(45) Date of Patent: Apr. 5, 2022

(54) HEALTH DATA COLLECTION DEVICE, HEALTH EVALUATION METHOD USING THE SAME, AND HEALTH EVALUATION SYSTEM INCLUDING THE HEALTH DATA COLLECTION DEVICE

(71) Applicant: ELECTRONICS AND TELECOMMUNICATIONS RESEARCH INSTITUTE, Daejeon (KR)

(72) Inventor: Han Young Yu, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 398 days.

(21) Appl. No.: 15/824,691

(22) Filed: Nov. 28, 2017

(65) Prior Publication Data
US 2018/0150610 A1 May 31, 2018

(30) Foreign Application Priority Data
Nov. 28, 2016 (KR) .................. 10-2016-0159651
Oct. 19, 2017 (KR) .................. 10-2017-0136123

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/0004* (2013.01); *A61B 5/02055* (2013.01);
(Continued)

(58) Field of Classification Search
CPC ........ G16H 50/20; G16H 40/67; G16H 40/63; G16H 50/30; A61B 5/7264;
(Continued)

(56) References Cited

U.S. PATENT DOCUMENTS

2005/0283053 A1* 12/2005 deCharms ............... A61B 5/055
600/300
2008/0162352 A1* 7/2008 Gizewski ............... G16H 40/60
705/50

(Continued)

FOREIGN PATENT DOCUMENTS

KR 10-0397188 B1 9/2003
KR 10-2009-0027027 A 3/2009
(Continued)

*Primary Examiner* — Robert A Sorey
*Assistant Examiner* — Kimberly A. Sass

(57) ABSTRACT

Provided are a health data collection device, a health evaluation system using this, and a health evaluation method including the health data collection device. The health data collection device includes a stimulation providing device, a bio signal measurement device, and a controller. The stimulation providing device provides stimulation such that a user changes from a stabilization state to a perturbation state. The bio signal measurement device measures a first bio signal in the stabilization state and a second bio signal in the perturbation state. The controller controls a stimulation providing device or a bio signal measurement device based on personal identification information. The controller generates physiological function data based on the first bio signal and the second bio signal. According to the inventive concept, bio-signals are measured using continuously changing personal identification information and stimulation, so data optimized for health state evaluation may be collected.

19 Claims, 19 Drawing Sheets

(51) Int. Cl.
*G16H 50/30* (2018.01)
*A61B 5/0205* (2006.01)
*G16H 40/67* (2018.01)
*G16H 40/63* (2018.01)
*A61B 5/0531* (2021.01)
*A61B 5/024* (2006.01)
*A61B 5/30* (2021.01)
*A61B 5/318* (2021.01)
*A61B 5/389* (2021.01)

(52) U.S. Cl.
CPC .......... *A61B 5/4884* (2013.01); *A61B 5/7264* (2013.01); *G16H 40/63* (2018.01); *G16H 40/67* (2018.01); *G16H 50/30* (2018.01); *A61B 5/02416* (2013.01); *A61B 5/0531* (2013.01); *A61B 5/30* (2021.01); *A61B 5/318* (2021.01); *A61B 5/389* (2021.01)

(58) Field of Classification Search
CPC . A61B 5/02055; A61B 5/4884; A61B 5/0004; A61B 5/0488; A61B 5/0531; A61B 5/0402; A61B 5/02416; A61B 5/04004; G06F 19/3418
See application file for complete search history.

(56) References Cited

U.S. PATENT DOCUMENTS

| | | | |
|---|---|---|---|
| 2016/0147960 A1 | 5/2016 | Kim et al. | |
| 2016/0147975 A1 | 5/2016 | Han et al. | |
| 2016/0253563 A1* | 9/2016 | Lam | G06F 11/0748 348/130 |

FOREIGN PATENT DOCUMENTS

| | | | | |
|---|---|---|---|---|
| KR | 10-1227415 B1 | 1/2013 | | |
| KR | 10-1466359 B1 | 11/2014 | | |
| KR | 10-1641455 B1 | 7/2016 | | |
| KR | 10-1661116 B1 | 9/2016 | | |
| WO | WO-2016134271 A1 * | 8/2016 | ......... A61N 1/36025 |

* cited by examiner

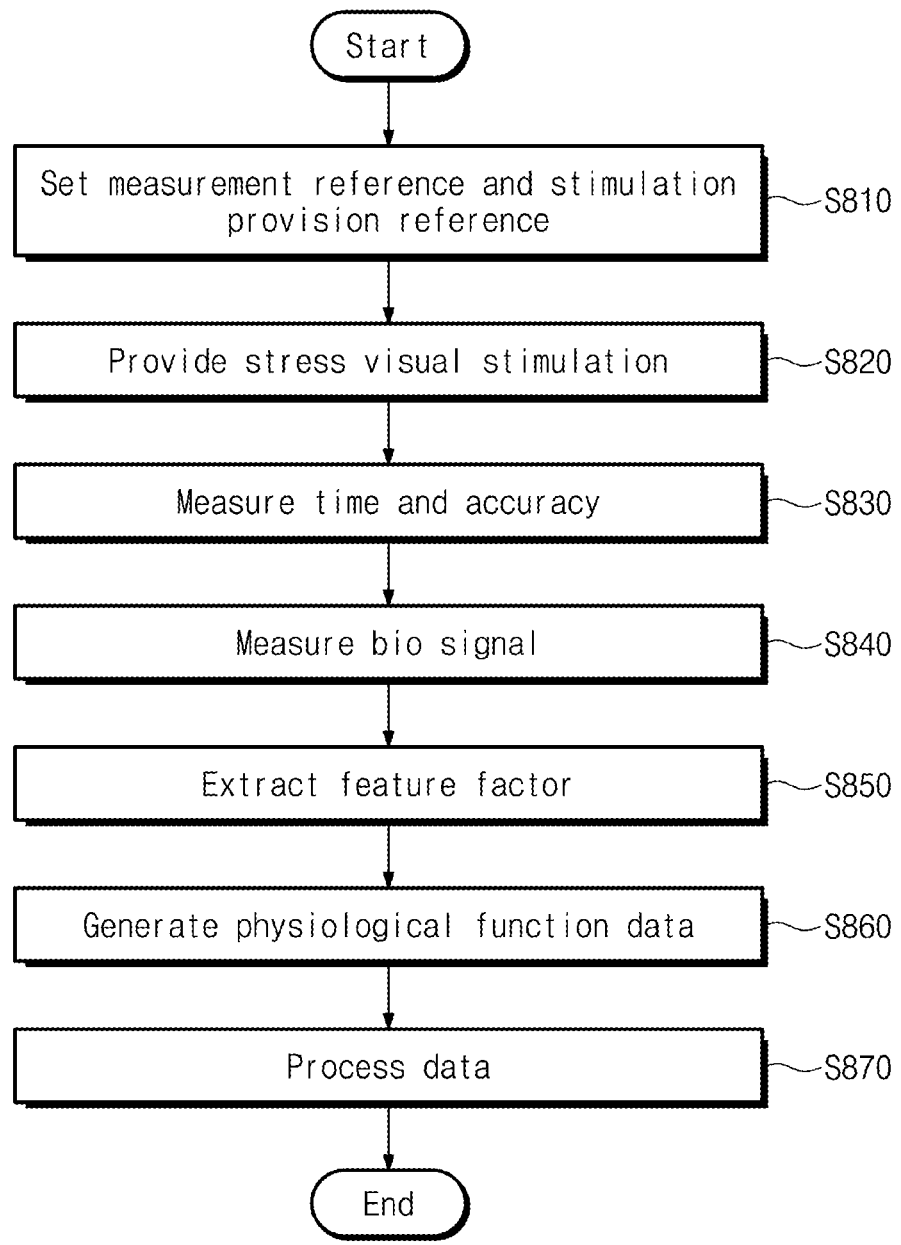

HEALTH DATA COLLECTION DEVICE, HEALTH EVALUATION METHOD USING THE SAME, AND HEALTH EVALUATION SYSTEM INCLUDING THE HEALTH DATA COLLECTION DEVICE

CROSS-REFERENCE TO RELATED APPLICATIONS

This U.S. non-provisional patent application claims priority under 35 U.S.C. § 119 of Korean Patent Application Nos. 10-2016-0159651, filed on Nov. 28, 2016, and 10-2017-0136123, filed on Oct. 19, 2017, the entire contents of which are hereby incorporated by reference.

BACKGROUND

The inventive concept relates to health state analysis and prediction, and more particularly, to a health data collection device, a health evaluation system using this, and a health evaluation method including the health data collection device.

The human health state is constantly changing. The health state changes mainly in the form of growth in childhood and adolescence, but the health state mainly changes in the form of aging in adolescence and old age. As a human life expectancy increases, there is a demand for healthy living by analyzing the variation of a health state such as the progress of aging.

With the development of medical technology, various technologies are being developed to analyze the body composition of the human body and examine the health. However, the analysis using the body composition of the human body is limited to the purpose of health examination. There are few technologies available to evaluate various health states, such as prediction of the progress of aging. In particular, there are few technologies available for analyzing and evaluating health states in a noninvasive way to predict the progress of aging. Therefore, there is a need for a method for evaluating various health states in a noninvasive way.

SUMMARY

The present disclosure provides a health data collection device, a health evaluation method, and a health evaluation system, which non-invasively evaluate a health state but collect health data optimized for health state evaluation.

An embodiment of the inventive concept provides a health data collection device including: an input device configured to receive personal information of a user; a stimulation providing device configured to provide a stimulation to allow the user in a stabilization state to be changed to a perturbation state; a bio signal measurement device configured to measure a first bio signal in the stabilization state and measure a second bio signal in the perturbation state; a controller configured to control the stimulation providing device and the bio signal measurement device depending on the personal information or personal identification information and generate physiological function data based on a change amount of the first bio signal and the second bio signal; and a communication device configured to receive the personal identification information patterned according to an accumulation of the physiological function data from a management server and transmit the physiological function data to the management server.

In an embodiment, the input device may receive the personal information including at least one of name, sex, age, and human body information of the user, and the human body information may include height, weight, fingerprint, iris, and pulse information or disease information of the user.

In an embodiment, the controller may control at least one of an intensity of the stimulation, a type of the stimulation, and a time point of providing the stimulation depending on the personal information or the personal identification information.

In an embodiment, the stimulation providing device may provide an electrical stimulation to the user, wherein the bio signal measurement device may measure a first bio signal before providing the electrical stimulation, a second bio signal while providing the electrical stimulation, and the first and second bio signals may include at least one of electrocardiogram, pulse wave, skin conductivity, skin temperature, and brain wave.

In an embodiment, the stimulation providing device may provide a pressure stimulation to the user, wherein the bio signal measurement device may measure a first bio signal before providing the pressure stimulation, a second bio signal while providing the pressure stimulation, and the first and second bio signals may include at least one of electrocardiogram, pulse wave, skin conductivity, skin temperature, and brain wave.

The stimulation providing device may include a sensory stimulation providing device for providing the user with a sensory stimulation including at least one of visual, auditory, olfactory, tactile, and taste, wherein the bio signal measurement device may measure the first bio signal before providing the sensory stimulation and measure the second bio signal while providing the sensory stimulation.

The sensory stimulation providing device may include a touch display for providing a visual stimulation to the user and recognizing a touch inputted in response to the visual stimulation, wherein the controller may generate information on a response based on the recognized touch, and generate physiological function data on memory, executive power, concentration, and stress based on the first and second bio signals and the information on the response.

In an embodiment, the health data collection device may further include a laser detection sensor for detecting a laser light irradiated in response to the sensory stimulation, wherein the controller may generate information on a response based on the detected laser light, and generate physiological function data on at least one of memory, executive power, concentration, and stress based on the first and second bio signals and the information on the response.

In an embodiment, the controller may set a bio signal measurement reference depending on the personal information or the personal identification information.

In an embodiment, the bio signal measurement device may further measure a third bio signal in a restored stabilization state after the perturbation state, wherein the controller may generate the physiological function data based on the first to third bio signals.

In an embodiment, the controller may generate the physiological function data based on at least one of a change amount of the second bio signal and the third bio signal and a change amount of the first bio signal and the third bio signal, and a change amount of the first bio signal and the second bio signal.

In an embodiment of the inventive concept, a health evaluation method includes: receiving, by a controller, personal information from an input device or receiving personal identification information corresponding to a user from a management server; setting, by the controller, a measurement reference of a bio signal measurement device and a stimulation provision reference of a stimulation providing device based on the personal information or the personal identification information; measuring, by the bio signal measurement device, a first bio signal from the user in a stabilization state according to the measurement reference; providing, by the stimulation providing device, a stimulation to the user according to the stimulation provision reference; measuring, by the bio signal measurement device, a second bio signal from the user in a perturbation state according to the measurement reference; and generating, by the controller, physiological function data based on the first bio signal and the second bio signal.

In an embodiment, the generating of the physiological function data may include: extracting, by the controller, a first feature factor from the first bio signal and extracting a second feature factor from the second bio signal; and extracting, by the controller, the physiological function data based on a change amount of the first feature factor and the second feature factor.

In an embodiment, the method may further include: providing, by a communication device, bio signal data generated by converting the first and second bio signals, stimulation data, feature factor data generated by converting first and second feature factors extracted from the first and second bio signals, and the physiological function data to the management server; classifying, by the management server, the physiological function data to generate health function data; and grouping, by the management server, the bio signal data, the stimulation data, the feature factor data, the physiological function data, and the health function data as visit data and storing the visit data.

In an embodiment, the method may further include comparing, by the management server, the visit data and previously-stored visit data to analyze a health variation and predict a health function.

In an embodiment, the method may further comprising comparing, by the management server, the visit data and previously stored visit data to generate the personal identification information.

In an embodiment, the method may further include measuring, by the bio signal measurement device, a third bio signal from the user according to the measurement reference after the providing of the stimulation is terminated, wherein the extracting the physiological function data may include comparing the first to third bio signals to extract the physiological function data.

In an embodiment of the inventive concept, a health evaluation system includes: a health data collection device configured to provide a stimulation to a user, measure a first bio signal from the user before providing the stimulation, measure a second bio signal from the user while providing the stimulation, extract a feature factor from the first and second bio signals according to a reference set based on personal identification information, and classify the feature factor by a physiological function to collect physiological function data; and a management server configured to analyze a health variation of the user and update the personal identification information based on the physiological function data and previously-stored physiological function data.

In an embodiment, the health data collection device may include: a stimulation providing device configured to provide the stimulation; a bio signal measurement device configured to measure the first bio signal and the second bio signal; and a controller configured to set a reference for extracting the feature factor based on the personal identification information to extract the feature factor and generate the physiological function data.

In an embodiment, the management server may include: a data storage unit configured to store the physiological function data by each use of the health data collection device; and a health function analysis device configured to compare the physiological function data with previously-stored physiological function data to generate health variation analysis data and the personal identification information.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIG. 19 is a view for explaining a process of collecting and processing physiological function data on stress.

DETAILED DESCRIPTION

In the following, embodiments of the inventive concept will be described in detail so that those skilled in the art easily carry out the inventive concept.

Figure 1:
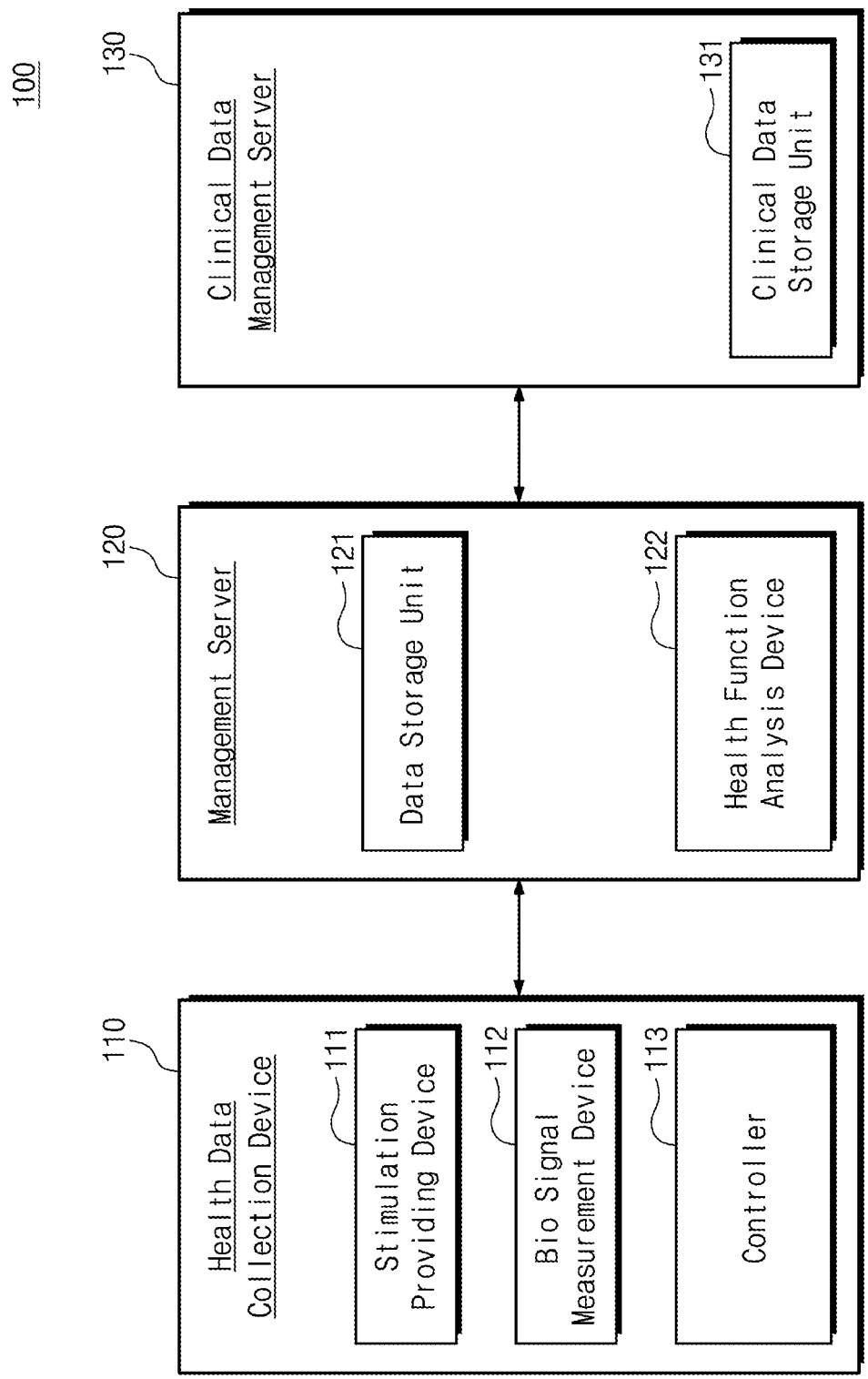
FIGS. 1 and 2 are block diagrams of a health evaluation system according to an embodiment of the inventive concept.

FIG. 1 is a block diagram of a health evaluation system according to an embodiment of the inventive concept. Referring to FIG. 1, a health evaluation system 100 includes a health data collection device 110, a management server 120, and a clinical data management server 130. The health data collection device 110 includes a stimulation providing device 111, a bio signal measurement device 112, and a controller 113. The management server 120 includes a data storage unit 121 and a health function analysis device 122. The clinical data management server 130 includes a clinical data storage unit 131.

The health data collection device 110 receives a bio signal from a user. The health data collection device 110 extracts a feature factor from the bio signal. The health data collection device 110 may classify the feature factors and generate physiological function data representing the physiological features of each organ of the human body. For example, the physiological function data may represent blood pressure, cardiac output, skin temperature, and so on. The health data collection device 110 may convert the bio signal into bio signal data and convert the extracted feature factor into feature factor data.

To analyze the health function of the user, the health data collection device 110 may provide bio signal data, feature factor data, and physiological function data to the management server 120. The health data collection device 110 may analyze the physiological function data to generate health function data related to a state in which the user performs a normal life. For example, the health function data may indicate aging progress or homeostasis of the human body. If the health function data is generated by the health data collection device 110, health function data may be provided to the management server 120. However, the embodiment is not limited to this, and the health function data may be generated by the health function analysis device 122 included in the management server 120. Details of bio-signal data, physiological function data, and health function data are described below.

The stimulation providing device 111 provides stimulation to the user. The user in a stabilization state may change to a perturbation state by the provided stimulus. The bio signal measured from the user in the stabilization state and the bio signal measured from the user in the perturbation state are different. Changes in the bio signal vary depending on the user's health state, i.e., the healthy state, the diseased state, and the health state's stage. That is, when the stimulation providing device 111 is used, the health function of the user may be more accurately and easily analyzed. The stimulation providing device 111 may provide electrical stimulation and pressure stimulation and may be implemented to provide various stimulations such as visual, auditory, olfactory, tactile, and taste.

The bio signal measurement device 112 measures a first bio signal from the user in the stabilization state and a second bio signal from the user in the perturbation state. The bio signal measurement device 112 may further measure a third bio signal from the user in the restored stabilization state after the perturbation state. Since the state of the human body changes by stimulation, the first bio signal and the second bio signal will be different. The difference between the first bio signal and the second bio signal may be an index of the user's health state.

The controller 113 controls the stimulation providing device 111 and the bio signal measurement device 112. In addition, the controller 113 may extract a feature factor from the bio signal measured by the bio signal measurement device 112 and generate physiological function data based on the extracted feature factor. The controller 113 may receive the user's personal information and generate physiological function data using the personal information. The controller 113 may determine the stimulation providing reference of the stimulation providing device 111 and the bio signal measurement reference of the bio signal measurement device 112 according to the user's personal information. In addition, the controller 113 may determine the reference for extracting the feature factor of the bio signal and the classification reference of the feature factor according to the personal information.

The controller 113 may be implemented in a computer system, e.g., as a computer readable medium. The controller 113 may include one or more of a processor, an input device, an output device, and a storage, each of which communicates through a bus. The processor may include a central processing unit (CPU) and an application processor. The processor executes processing instructions stored in the storage. For example, the processor may execute processing instructions for extracting the feature factor of the bio signal. The processor may execute processing instructions for generating physiological function data in response to the personal information (or personal identification information provided by the management server 120). The storage may include various forms of volatile or non-volatile storage media. The storage may store bio signal data, feature factor data, and physiological function data.

The management server 120 receives bio signal data, feature factor data, and physiological function data from the health data collection device 110. In addition, the management server 120 may receive personal information from the health data collection device 110. The data storage unit 121 may store bio signal data, feature factor data, physiological function data, health function data, and personal information. The bio signal data, the feature factor data, and the health function data may be grouped and stored as one visit data. The visit data may be accumulated and stored in the data storage unit 121 for each use time of the health data collection device 110.

The management server 120 may be implemented in a computer system, e.g., as a computer readable medium. The management server 120 may include one or more of a processor, an input device, an output device, and a storage, each of which communicates through a bus. The management server 120 may also include a network interface for communicating with the health data collection device 110. The processor may include a central processing unit (CPU) and an application processor. The processor executes processing instructions stored in the storage. For example, the health function analysis device 122 may be implemented in the processor. The storage may include various forms of volatile or non-volatile storage media.

The health function analysis device 122 may analyze the health function of the user using the visit data stored in the data storage unit 121. The health function analysis device 122 may analyze the health variation by comparing the visit data stored at each use time in the health data collection device 110. The health function analysis device 122 may classify and analyze changes in visit data to pattern the health trend of the user. This patterned health trend may represent one image data. Such image data may be personal identification information. The personal identification information may be stored in the data storage unit 121. The personal identification information may be updated and stored in the data storage unit 121 whenever the health function is analyzed.

The personal identification information may be provided to the health data collection device as personal information when the user later uses the health data collection device 110. The health data collection device 110 may provide stimulation to a user and measure a bio signal according to personal identification information. The health data collection device 110 may extract the feature factor from the bio signal and generate the physiological function data according to the personal identification information. The degree of responding to stimulation, the degree of maintaining a stabilization state, and the reference for extracting feature factors from a bio signal are all different for each user. When the personal identification information updated depending on the number of visits, visit data considering user's unique human characteristics may be collected. Thus, the accuracy and efficiency of the health function analysis may be improved.

The clinical data management data server 130 may provide clinical data to the management server 120 to improve the accuracy of the health function analysis. In addition to the data generated by the health data collection device 110, clinical information generated in a hospital or the like may be stored in the clinical data storage unit 131. For example, clinical data may include drug prescription information, blood test result information, medical imaging information, medical information, diagnostic result information, family history information, or disease information. The clinical data may be additionally stored in the data storage unit 121 together with the visit data of the user. The health function analysis device 122 may further analyze the health function of the user by considering the clinical data additionally.

The clinical data management data server 130 may be implemented in a computer system, e.g., as a computer readable medium. The clinical data management data server 130 may include one or more of a processor, an input device, an output device, and a storage, each of which communicates through a bus. The clinical data management data server 130 may also include a network interface for communicating with the management server 120. The processor may include a central processing unit (CPU) and an application processor. The processor executes processing instructions stored in the storage. The storage may include various forms of volatile or non-volatile storage media.

Figure 2:
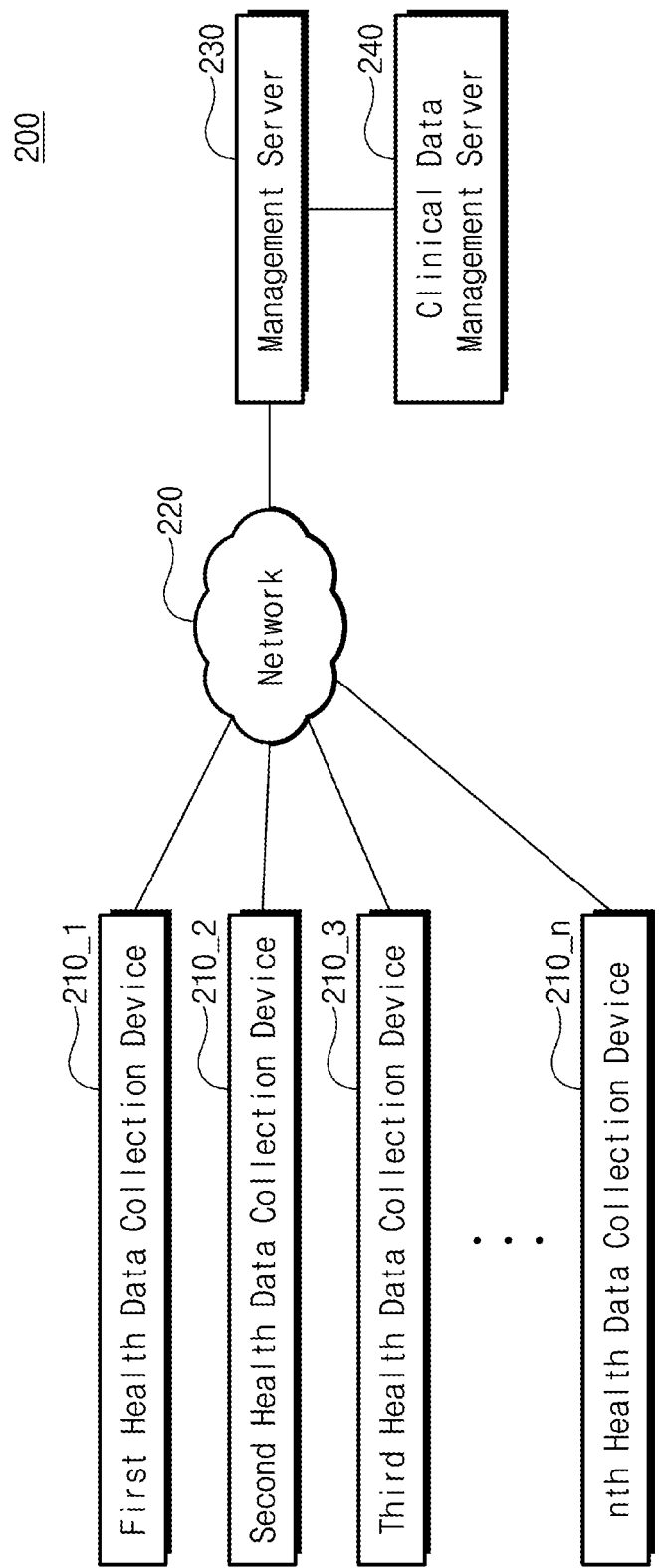

FIG. 2 is a block diagram of a health evaluation system according to an embodiment of the inventive concept. Referring to FIG. 2, a health evaluation system 200 includes first to nth health data collection devices 210_1 to 210_n, a network 220, a management server 230, and a clinical data management server 240. The management server 230 and the clinical data management server 240 may have the same configuration as the management server 120 and the clinical data management server 130 of FIG. 1, respectively, and may perform the same functions.

The first to nth health data collection devices 210_1 to 210_n may have the same configuration as the health data collection device 110 of FIG. 1 and may perform the same function. The first to nth health data collection devices 210_1 to 210_n may be disposed at different locations. A user may use any one of the first to nth health data collection devices 210_1 to 210_n and later use another one of the first to nth health data collection devices 210_1 to 210_n. The management server 230 may store visit data, which is received from health data collection devices at different places, at each time over time. That is, the integrated management server 230 may analyze and predict health functions over time using bio signals measured at different times and at different places.

The network 220 may provide the management server 230 with data received from the first to nth health data collection devices 210_1 to 210_n. The data received from the network 220 may include bio signal data, stimulation data, feature factor data, physiological function data, and health function data. Also, the data received from the network 220 may include personal information. The network 220 may receive personal identification information from the management server 230 and provide the received personal identification information to any one of the first to nth health data collection devices 210_1 to 210_n. The network 220 may provide data communication between the first to nth health data collection devices 210_1 to 210_n and the management server 230 in a wire or wireless manner.

Each of the first to nth health data collection devices 210_1 to 210_n may have unique device identification information. Each of the first to nth health data collection devices 210_1 to 210_n may additionally provide device identification information to the management server 230. The management server 230 may determine the reliability of the data based on the device identification information. The management server 230 may analyze the data in consideration of the geographical characteristics according to the location of the device identification information. For example, the management server 230 may receive environment information on a region where the health data collection device is located from a separate external server. The environment information may include climate information such as temperature, humidity, atmospheric pressure, or GPS coordinate information. By using this environment information, the management server 230 may consider the variation of a health function according to environmental factors.

Figure 3:
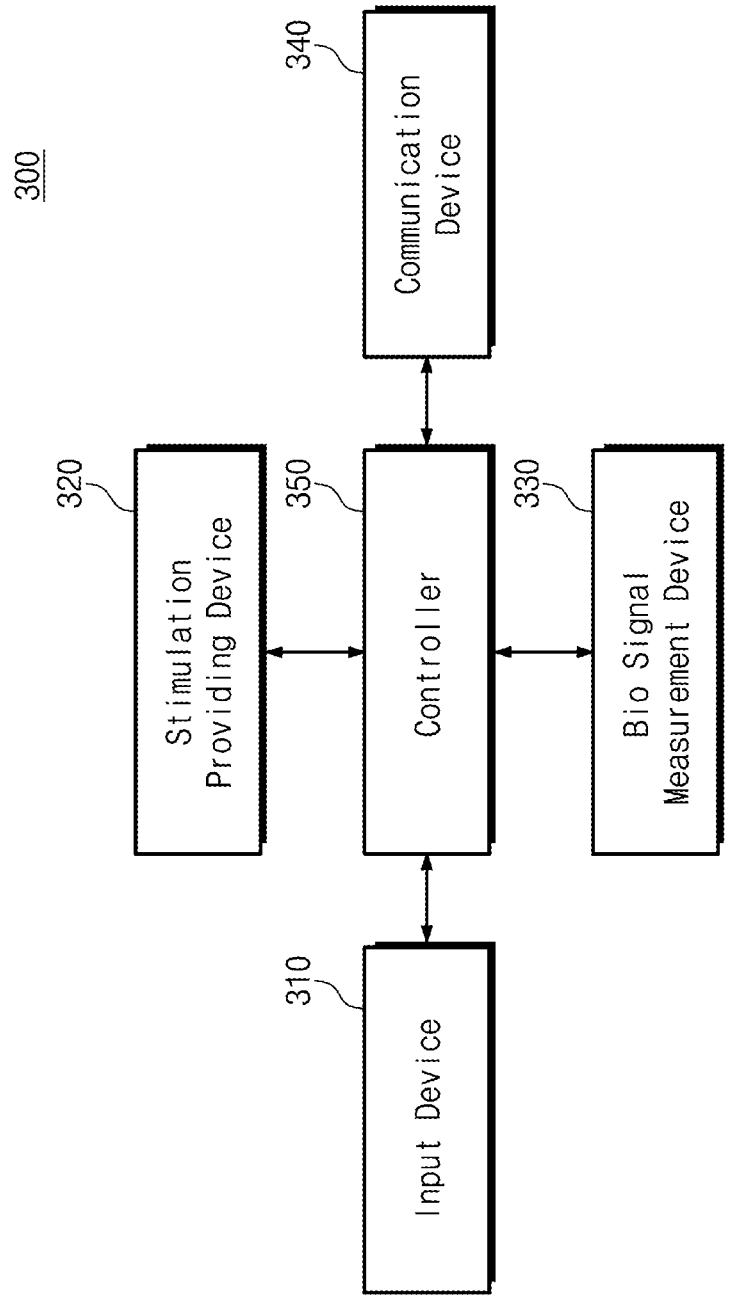
FIGS. 3 and 4 are block diagrams of a health data collection device according to an embodiment of the inventive concept.

FIG. 3 is a block diagram of a health data collection device according to an embodiment of the inventive concept. Referring to FIG. 3, a health data collection device 300 includes an input device 310, a stimulation providing device 320, a bio signal measurement device 330, a communication device 340, and a controller 350. The health data collection device 300 may be the health data collection device 110 of FIG. 1 or the first to nth health data collection devices 210_1 to 210_n of FIG. 2.

The input device 310 may be configured to receive an input signal from a user. For example, the input device 310 may include a keypad, a touch screen, a touch pen, a microphone, or the like. The input device 310 may provide an input signal to the controller 350. The input signal may be personal information corresponding to the user or a response signal to the stimulation provided by the health data collection device 300. Also, the input signal may be a progress signal inputted in response to the guidance information provided by the health data collection device 300 to the user.

The personal information may include at least one of the user's name, sex, age, human body information, fingerprint, iris, pulse information, and personal identification information. The human body information may include at least one of the user's height, weight, and disease information. When the user first uses the health data collection device 300, the input device 310 may receive personal information. The stimulation providing device 320, the bio signal measurement device 330, and the controller 350 may be driven depending on personal information before the visit data on the user is accumulated in the management server. For example, the controller 350 may receive personal information from the input device 310, including the user's gender and age information. The controller 350 may control the stimulation providing device 320 and the bio signal measurement device 330 according to the average stimulation response degree, degree of maintaining the stabilization state, or extraction criterion of the feature factor of the corresponding gender and age to generate physiological function data.

Thereafter, when the user uses the health data collection device 300, the input device 310 may receive personal identification information. At this time, the input device 310 may not receive a separate name, sex, age, and human body information. Also, as the user continues to use the health data collection device 300, patterned health trends may be stored in the management server as personal identification information. In this case, the user may be identified in the process of measuring the bio signal without providing personal identification information to the input device 310.

The stimulation providing device 320 provides stimulation such that the user changes from a stabilization state to a perturbation state. The stimulation providing device 320 may provide sensory stimulation such as weak electrical stimulation, pain stimulation, pressure stimulation, or visual, which is weak and harmless to the human body. The stimulation providing device 320 may include a plurality of stimulation providing devices that provide different stimulations. A plurality of stimulation providing devices may provide a user with various kinds of stimulations in combination or selectively. According to the stimulation provided by the stimulation providing device 320, the corresponding bio signal is measured and physiological function data is generated. For example, if the stimulation providing device 320 provides the user with electrical stimulation, the pulse wave, electrocardiogram, brain wave, or skin conductivity may be measured. Physiological function data such as stress may be generated based on pulse wave, electrocardiogram, brain wave, or skin conductivity.

The stimulation providing device 320 may provide stimulation to the user depending on the personal information. The response to stimulation may vary from person to person. For example, older users may be insensitive to electrical stimulation, and the intensity of stimulation or the duration of stimulation may be adjusted to reflect personal information. In addition, the bio signal required by an individual may be different. Thus, the type of stimulation provided according to personal information may be determined. For example, in order to generate physiological function data related to memory, the stimulation providing device 320 may include a display that provides visual stimulation. The stimulation providing device 320 may determine the visual stimulation displayed by the display by reflecting personal information. When receiving personal information of a user with low cognitive abilities, the stimulation providing device 320 may provide a simpler visual stimulation.

The bio signal measurement device 330 measures the first bio signal from the user in a stabilization state before the stimulation providing device 320 provides stimulation. Then, the stimulation providing device 330 may provide stimulation to the user with a specified time interval according to the personal information. The bio signal measurement device 330 may continuously measure the second bio signal from the user in a perturbation state when the stimulation providing device 320 provides stimulation. Changes in the first bio signal and the second bio signal are used to analyze the user's health function. For example, if the second bio signal is a bio signal measured at the start time point of stimulation, the amount of changes in the first bio signal and the second bio signal may be an index to determine the degree of response to user's stimulation. Also, the size of the first bio signal and the second bio signal itself may be used to analyze the health of the user.

The stimulation may provide a reference of the measured bio signal change. It is difficult to distinguish whether the changes in the measured signal is due to stimulation or a routine changes in the general case of measuring bio signals without providing a reference for stimulation. The health data collection device 300 provides a stimulation that forces changes in the bio signal and sets the reference for stimulation based on personal information. The bio signal measurement device 330 may measure bio signals different to each individual based on personal information and set a reference point (e.g., a reference time point or a reference frequency) for measuring a bio signal change different to each individual. That is, in the second bio signal, the signal change due to the stimulation providing device 320 and the signal change due to other unspecified factors may be easily distinguished and classified. The second bio signal may be normalized by the reference set according to the personal information.

The stimulation may also provide a reference for determining the error of a measured bio signal. Depending on the reference point set for measuring the bio signal, changes in the bio signal other than the reference point may be recognized as noise. For example, the bio signal may be expressed by the action of a nerve system such as a peripheral nerve system. In addition, an autonomic nerve system, which is operated by sympathetic nerve and parasympathetic nerve, in the peripheral nerve system is affected by the activity of a central nerve system. When the central nerve system shows a variation phenomenon, after a predetermined time delay, the corresponding variation of the peripheral nerve system is measured in the bio signal. That is, a predetermined time delay is reflected to set the reference point, and the change of the bio signal at the time point beyond the reference point may be regarded as noise.

Stimulation may be non-periodically repeated and provided. In this case, the bio signal measurement device 330 may measure bio signals by non-periodic stimulations. Changes in bio signals by non-periodic stimulations may be used to generate physiological function data related to stimulation adaptation.

The bio signal measurement device 330 may continue to measure the bio signal even after the stimulation providing device 320 terminates the provision of the stimulation. That is, the bio signal measurement device 330 may measure the third bio signal from the restored user after the perturbation state by stimulation. The first bio signal before the stimulation is provided and the third bio signal after the stimulation is provided may be compared with each other. With the provision of stimulation, the bio signal may change drastically. When stimulation is removed, changes in the bio signal occur more slowly than changes due to stimulation. That is, the human body does not progress rapidly to the stabilization state due to the adaptation time for stimulation. That is, the change from the second bio signal to the third bio signal may be an additional factor for analyzing the user's health function. The third bio-signal may be used for health function evaluation about the degree that a user returns to its original stabilization state after stimulation is terminated.

The communication device 340 provides data generated by the health data collection device 300 to the management server. The data generated by the health data collection device 300 may include bio signal data, stimulation data, feature factor data, physiological function data, and health function data. The communication device 340 may provide the management server with the personal information provided from the input device 310. The communication device 340 may provide data to the network 220 of FIG. 2 in a wire or wireless way. In addition, the communication device 340 may receive personal identification information from the management server and provide it to the controller 350.

The controller 350 controls the input device 310, the stimulation providing device 320, the bio signal measurement device 330, and the communication device 340. The controller 350 may function as a central control device for controlling the overall data collection and data processing of the health data collection device 300. The controller 350 may be implemented with a dedicated circuit such as an Application Specific Integrated Circuit (ASIC). Alternatively, the controller 350 may be implemented with software or firmware.

Under the control of the controller 350, the input device 310 may receive personal information, or the communication device 340 may receive personal identification information from the management server. The controller 350 sets a stimulation provision reference based on personal information or personal identification information. The controller 350 may generate stimulation data for controlling stimulation providing device 320 according to a stimulation provision reference. The controller 350 may use stimulation data to control the intensity or type of stimulation provided by the stimulation providing device.

The controller 350 sets a measurement reference of the bio signal measurement device 330 based on personal information or personal identification information. The bio signal measurement device 330 may measure the first to third bio signals according to a measurement reference set by the controller 350. The controller 350 may remove noise of the first to third bio signals based on the set measurement reference. The controller 350 may convert the first to third bio signals into bio signal data for storing it in the management server. The first to third bio signals may include various kinds of feature factors such as pulse wave, electrocardiogram, or brain wave. The controller 350 may extract feature factors from the first to third bio signals.

The controller 350 generates physiological function data based on the extracted feature factors. The controller 350 may classify and combine feature factors according to a plurality of physiological functions. For example, the controller 350 may control the stimulation providing device 320 to provide pressure stimulation. The controller 350 may control the bio signal measurement device 330 to measure electromyogram. The controller 350 extracts the feature factors corresponding to the electromyogram and analyzes the variation of the electromyogram according to the stimulation. The controller 350 may generate physiological function data related to changes in the muscles as the electromyogram changes. The specific types of physiological function data and the process of generating them will be described below with reference to FIG. 10.

The controller 350 may convert the extracted feature factors into feature factor data for storing it in the management server. The controller 350 may provide bio signal data, stimulation data, feature factor data, and physiological function data to the communication device 340 for storing them in the management server. The controller 350 may provide data on the time of additionally providing stimulation or the time of measuring bio signals to the communication device 340.

Figure 4:
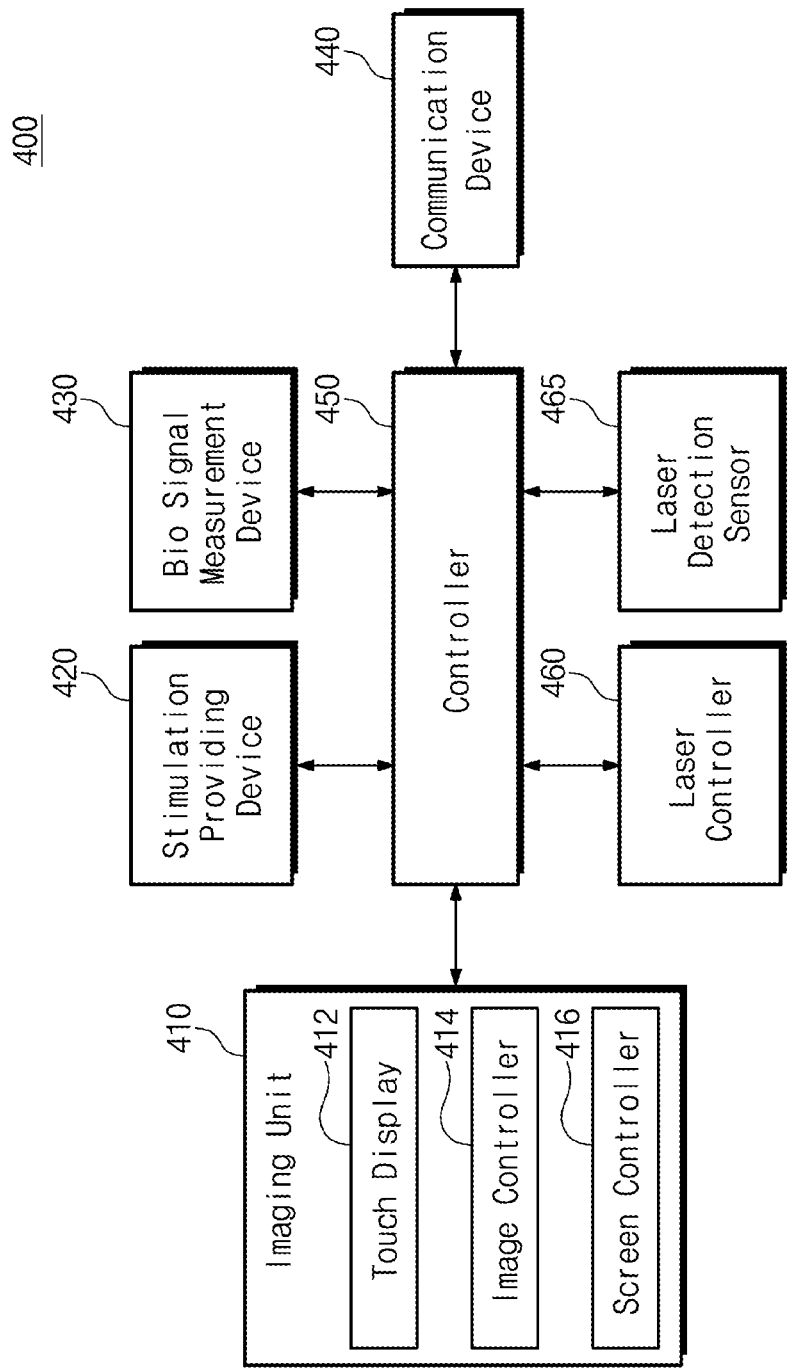

FIG. 4 is a block diagram of a health data collection device according to an embodiment of the inventive concept. Referring to FIG. 4, a health data collection device 400 includes an imaging unit 410, a stimulation providing device 420, a bio signal measurement device 430, a communication device 440, a controller 450, a laser controller 460, and a laser detection sensor 465. The health data collection device 400 may be the health data collection device 110 of FIG. 1 or the first to nth health data collection devices 210_1 to 210_n of FIG. 2. The stimulation providing device 420, the bio signal measurement device 430 and the communication device 440 may be the stimulation providing device 320, the bio signal measurement device 330 and the communication device 340 of FIG. 3, respectively.

The imaging unit 410 may include a touch display 412, an image controller 414, and a screen controller 416. The touch display 412 senses a user's touch and generates a touch signal. The touch display 412 may interact with a user. The touch display 412 may provide a guidance image to the user. Alternatively, the touch display 412 may provide visual stimulation to the user. The touch display 412 may provide a touch signal to the controller 450 in response to a guidance image or visual stimulation. The touch signal may be personal information, may be a response signal to stimulation, and may be a progressive signal that is inputted in response to the guidance information.

The image controller 414 may control an image displayed on the touch display 412. For example, the image controller 414 may receive image data from the controller 450, convert the image data to a data voltage, and provide it to the touch display 412. The screen controller 416 may control an image displayed on an external screen. The health data collection device 400 may provide stimulation to a user using an external screen and perform use guidance. In response to visual stimulation displayed by an external screen, a user may react to the stimulation by irradiating the screen with laser light.

The laser controller 460 may control a laser pointer (not shown) used by a user in response to the stimulation displayed on a screen or the stimulation provided by the stimulation providing device 420. The laser controller 460 may control the irradiation of laser light or the amount of light. The laser detection sensor 465 may detect laser light that reaches a screen or is reflected by a screen. For example, in response to the visual stimulation provided by the screen, the user may change the irradiation direction of the laser light. The laser detection sensor 465 may measure the travel path or the location of the laser light.

The controller 450 may generate additional data related to the nerve response speed using the measured travel path of the laser light. For example, the touch display 412 or screen may provide a user with visual stimulation that requests a specific instruction from a user. At this time, the stimulation providing device 420 may include a speaker that provides auditory stimulation. The controller 450 may receive signals provided by a user from the touch display 412 or the laser detection sensor 465 in response to visual or auditory stimulation. In addition, the controller 450 may measure bio signals according to visual or auditory stimulation from the bio signal measurement device 430. Using the user-provided signal and the measured bio signal, the controller 450 may generate physiological function data.

Figure 5:
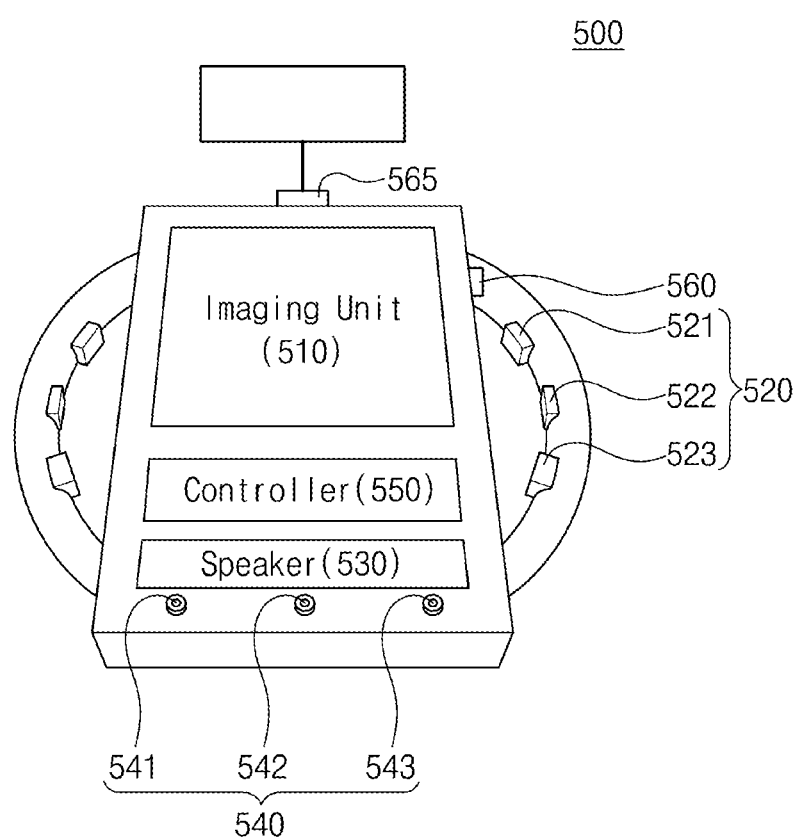
FIGS. 5 to 7 are views illustrating a health data collection device according to an embodiment of the inventive concept.

FIG. 5 is a view illustrating a health data collection device according to an embodiment of the inventive concept. Referring to FIG. 5, a health data collection device 500 includes an imaging unit 510, a bio signal measurement device 520, a speaker 530, a connector 540, a controller 550, a laser switch 560, and a laser pointer 565. The health data collection device 500 may be the health data collection device 110 of FIG. 1 or the first to nth health data collection devices 210_1 to 210_n of FIG. 2. The imaging unit 510 may include a touch screen. The imaging unit 510 may display guidance information of the health data collection device 500. The imaging unit 510 may display information related to changes in the bio signal due to stimulation.

The bio signal measurement device 520 may sense a plurality of bio signals. Illustratively, in FIG. 5, the bio signal measurement device 520 includes first to third sensors 521 to 523. The first sensor 521 may be a sensor for sensing skin conductivity (e.g., electrodermal activity (EDA)). The second sensor 522 may be a sensor for detecting pulse wave (e.g., photoplethysmogram (PPG)). The third sensor 523 may be a sensor for sensing skin temperature. However, the embodiment is not limited thereto, and the bio signal measurement device 520 may be a sensor for sensing various bio signals such as electromyogram (EMG), skin impedance, electrocardiogram (ECG), and pulse wave (e.g., PPG). Also, a stimulation providing device that provides electrical stimulation or pressure stimulation to a user may be disposed adjacent to the bio signal measurement device 520.

The bio signal measurement devices 520 may be disposed on the left and right sides of the imaging unit 510. Handles may be disposed on the left and right sides of the imaging unit 510, and the bio signal measurement device 520 may be disposed on the handles. The bio signal measurement device 520 may be in contact with the user's hand. The bio signal measurement device 520 may measure bio signals from the user's left and right hands. Thus, the user's left-right balance may be analyzed using the bio signal measurement device 520. For example, using the physiological function data generated by the symmetrical health data collection device 500, the left and right imbalances of the nerve system and the left and right activity of the central nerve system may be analyzed. Also, by analyzing ECG and pulse wave, homeostasis of human body according to cardiac activity may be analyzed.

The speaker 530 may provide auditory stimulation to the user. That is, the speaker 530 may function as a stimulation providing device. Also, the speaker 530 may provide a guidance voice to the user. The speaker 530 may provide information to the user at the same time as the imaging unit 510, or may provide stimulation to the user. The connector 540 may be configured to be connected to other electronic devices. The connector 540 may be connected to a sensor that senses other bio signals to measure a bio signal that is difficult to be measured from the hand. For example, the connector 540 may be connected to an ECG detection electrode attached to the chest to measure an ECG. Alternatively, the connector 540 may be connected to a microphone for receiving a user's voice.

The connector 540 may include a plurality of connectors 541 to 543. Illustratively, in FIG. 5, the connector 540 includes the first to third connectors 541 to 543. The first to third connectors 541 to 543 may be connected to a separate stimulation providing device as well as a separate bio signal measurement device. For example, the connector 540 may be connected to an earphone that may provide auditory stimulation. Alternatively, the connector 540 may be connected to an electrical stimulation providing device or a pressure stimulation providing device. The first connector 541 and the third connector 543 may be disposed to be symmetrical with respect to the second connector 542 as a reference. For example, the first connector 541 may be connected to the left brain electroencephalogram (EEG) detection electrode, and the third connector 543 may be connected to the right brain EEG detection electrode. Although not specifically shown in the drawing, the health data collection device 500 may include a short range communication device for receiving a bio signal wirelessly, without electrically connecting to a connector.

The controller 550 may control devices connected to the imaging unit 510, the bio signal measurement device 520, the speaker 530, and the connector 540. The laser switch 560 may be a switch that controls the operation of the laser pointer 565. The laser pointer 565 may generate laser light to be irradiated to an external target. The user may adjust the direction and location of the laser light by moving the health data collection device 500 according to the instructions of the imaging unit 510 or the speaker 530. The health data collection device 500 may sense the adjusted laser light. The health data collection device 500 may generate physiological function data related to the nerve response in consideration of the path and speed of the laser light.

The health data collection device 500 may further include a vibration generation device that may be used for health function analysis together with the laser pointer 565. The vibration generation devices may cause hand tremors. When hand tremor occurs, the ability of the user to adjust the location of the laser irradiated to the external screen may be measured. Specifically, depending on the degree of aging of the human body or the degree of health of the nerve system, the time during which the laser beam may be held on the target in a vibrating state changes. Accordingly, the controller 550 may generate the physiological function data in consideration of the time for holding the laser light on the target.

Figure 6:
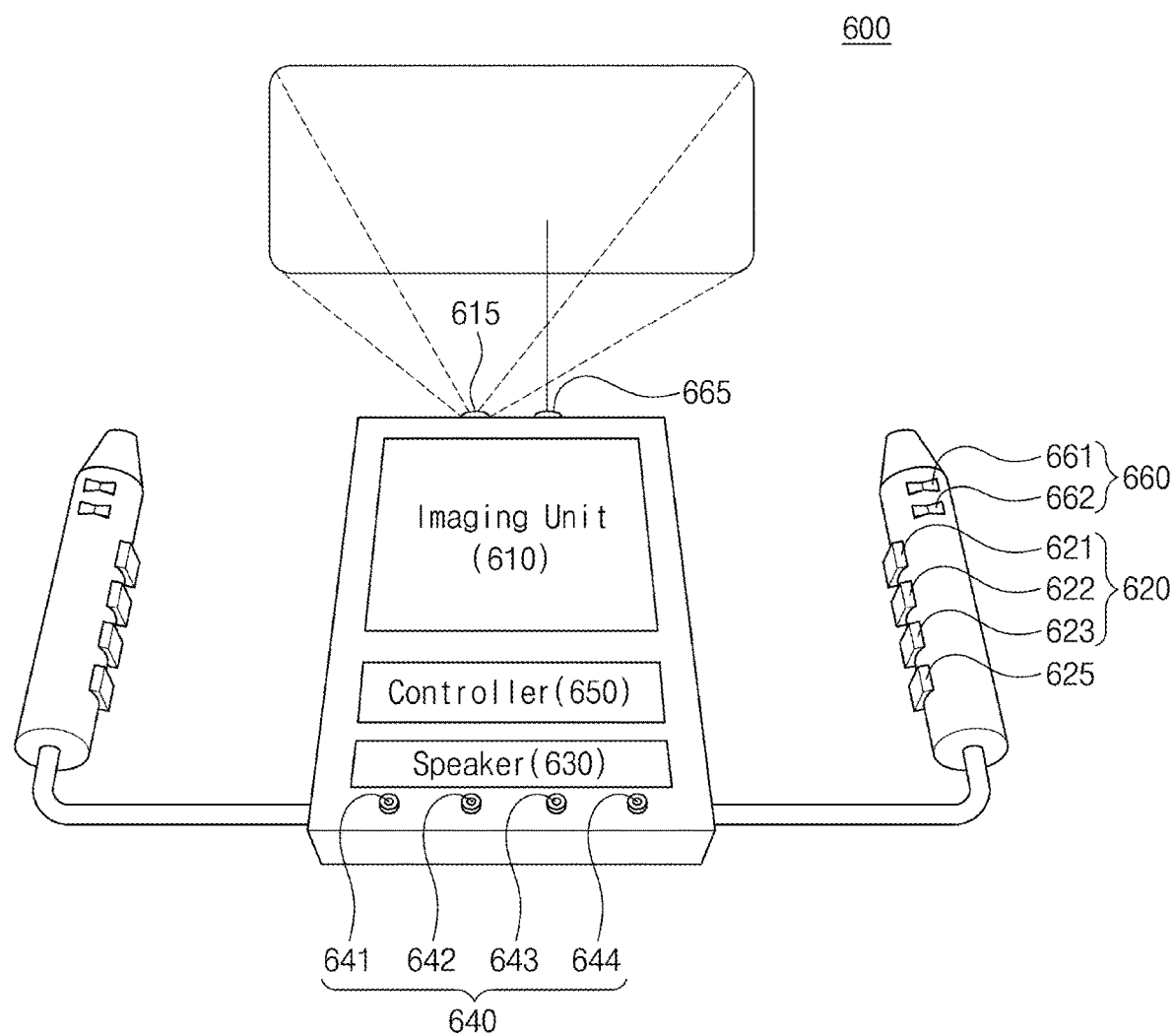

FIG. 6 is a view illustrating a health data collection device according to an embodiment of the inventive concept. Referring to FIG. 6, a health data collection device 600 includes an imaging unit 610, a projector 615, a bio signal measurement device 620, a stimulation providing device 625, a speaker 630, a connector 640, a controller 650, a control device 660, and a laser detection sensor 665. The health data collection device 600 may be the health data collection device 110 of FIG. 1 or the first to nth health data collection devices 210_1 to 210_n of FIG. 2.

The imaging unit 610, the speaker 630, and the controller 650 may be identical to the imaging unit 510, speaker 530, and controller 550 of FIG. 5, respectively. The bio signal measurement device 620 may include first to third sensors 621 to 623. The first to third sensors 621 to 623 may be the same as the first to third sensors 521 to 523 of FIG. 5. The stimulation providing device 625 may be an electrical stimulation providing device that provides electrical stimulation to a user. The connector 640 may include first to fourth connectors 641 to 644. The connector 640 may perform the same function as the connector 540 of FIG. 5.

The projector 615 may provide an image displayed on an external screen. The image provided by the projector 615 may be a guidance image. Alternatively, the image provided by the projector 615 may provide visual stimulation to the user. That is, the projector 615 may function as a stimulation providing device. Visual stimulation may optionally be provided to the user using the imaging unit 610 or the projector 615.

The control device 660 may include a light control device 661 and a touch control device 662. The control device 660 may be disposed adjacent to the handle on which the first to third sensors 621 to 623 are disposed. The light control device 661 may use the projector 615 to control the handle to perform the function of the laser pointer when stimulation is provided to the user. At this time, the laser detection sensor 665 may sense laser light. The touch control device 662 may control the handle to perform the function of the touch pen by using the imaging unit 610 when stimulation is provided to the user.

Figure 7:
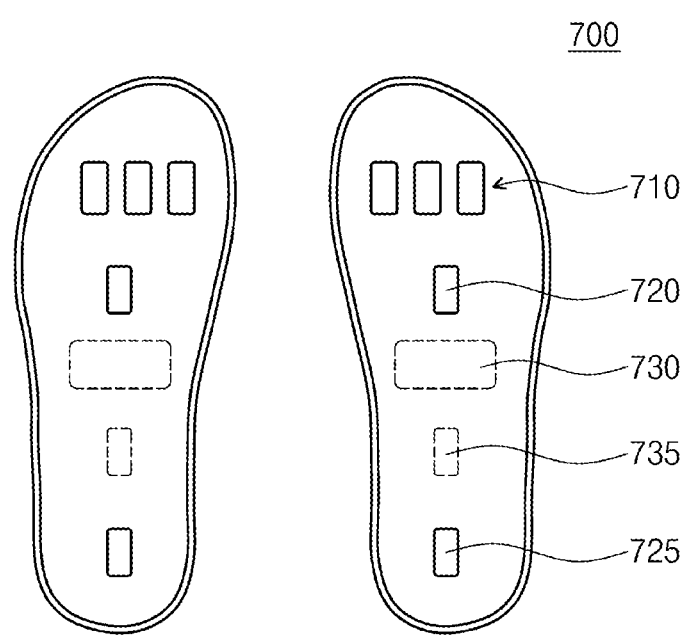

FIG. 7 is a view illustrating a health data collection device according to an embodiment of the inventive concept. Referring to FIG. 7, a health data collection device 700 includes a bio signal measurement device 710, a first stimulation providing device 720, a second stimulation providing device 725, a controller 730, and a three-axis acceleration sensor 735. The health data collection device 700 may be the health data collection device 110 of FIG. 1 or the first to nth health data collection devices 210_1 to 210_n of FIG. 2.

The health data collection device 700 may provide stimulation and contact the user's feet to measure bio signals. For this, the health data collection device 700 may have an insole shape in contact with the sole of the user. The health data collection device 700 may be implemented in a shoe shape. The health data collection device 700 may provide stimulation to the lower half of the user and measure the bio signal of the lower half. The health data collection device 700 may be used with the health data collection device 500 or 600 of FIG. 5 or FIG. 6. That is, the health data collection device 500 or 600 of FIG. 5 or 6 measures the bio signal of the upper half body, and the health data collection device 700 of FIG. 7 may measure the bio signal of the lower half body. The health data collection device 700 may communicate with the health data collection device 500 or 600 of FIG. 5 or 6 in a wire or wireless way, and may receive power from the same power supply device. Alternatively, the health data collection device 700 may further include a separate battery that may be charged and replaced.

The bio signal measurement device 710 may measure the bio signal before stimulation is provided, while stimulation is provided, and after stimulation is provided. The bio signal measurement device 710 may sense skin conductivity, pulse wave, or skin temperature. When the health data collection device 700 is used with the health data collection devices 500 or 600 of FIG. 5 or 6, the bio signals generated in each health data collection device may be compared. In addition, the health data collection device 700 may measure the bio signal measured in both feet, so that the left and right balance of the lower half body may be analyzed.

The first stimulation providing device 720 and the second stimulation providing device 725 provide stimulation to a user. The stimulation providing device 720 and the second stimulation providing device 725 may be used to provide stimulation to various parts of the user. For example, the first stimulation providing device 720 and the second stimulation providing device 725 may provide pressure stimulation. If pressure is provided to the user, fine pain may be caused to the user. The bio signal measurement device 710 may measure the bio signal according to the response of the peripheral nerve system and the central nerve system by pressure stimulation. The health data collection device 700 may further include a plurality of pressure sensors. The pressure sensor may be used to analyze the weight concentration of the human body.

The controller 730 controls the bio signal measurement device 710, the first stimulation providing device 720, and the second stimulation providing device 725. The three-axis acceleration sensor 735 may be used to remove the noise of the bio signal generated by the user's motion. For example, according to the provision of stimulation, the three-axis acceleration sensor 735 may sense the change, and only one bio signal of the measured bio signals may be specifically changed. At this time, the controller 730 may determine that the change of the bio signal is not the change of the bio signal by the nerve system but is the noise due to the motion of the user. In particular, unlike hands, feet have a body structure that is difficult to be fixed at the bio signal measurement device 710. The three-axis acceleration sensor 735 may improve the reliability of the stimulation provision from the health data collection device 700 and the reliability of the measured bio signal.

Figure 8:
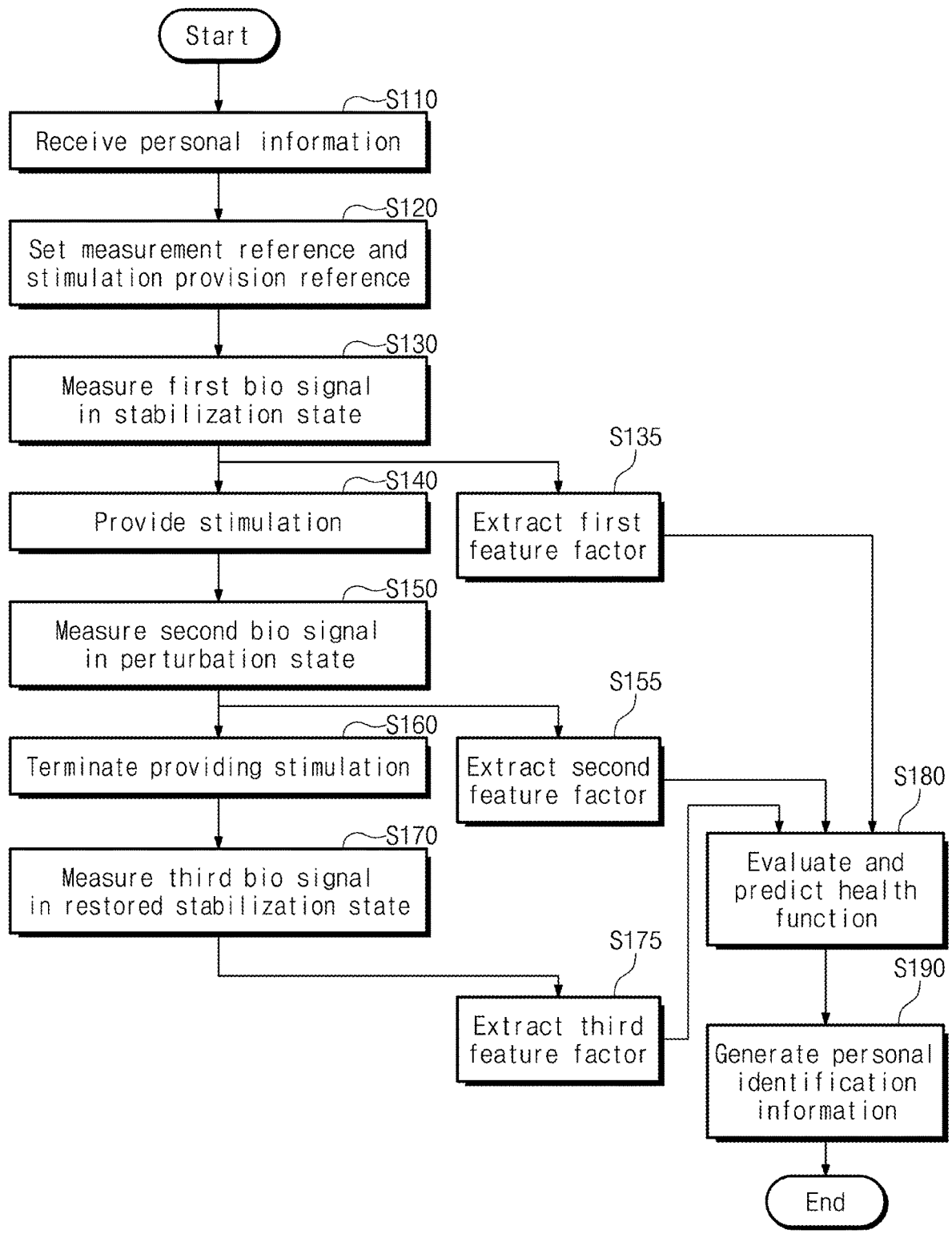
FIG. 8 is a flowchart of a health evaluation method according to an embodiment of the inventive concept.

FIG. 8 is a flowchart of a health evaluation method according to an embodiment of the inventive concept. The health evaluation method may be performed in the health evaluation system 100 of FIG. 1 or the health evaluation system 200 of FIG. 2. Also, some operations of the health evaluation method shown in FIG. 8 may be performed in any one of the health data collection devices 300 to 700 of FIGS. 3 to 7. Hereinafter, the health evaluation method will be described in correspondence with the components of FIG. 1.

In operation S110, the health data collection device 110 receives personal information. When the user first uses the health data collection device 110, the health data collection device 110 may receive personal information including the name, sex, and human body information from a user. Thereafter, when the user uses the health data collection device 110, the health data collection device 110 does not receive any personal information from the user but uses the personal identification information stored in the management server 120 to identify the user.

When the health data collection device 110 receives personal information or a user is identified using personal identification information, the health data collection device 110 provides guidance information to the user. The guidance information may include information related to the overall progress of a health function evaluation method. In addition, the guidance information may include contents for obtaining consent related to providing specific stimulation to a user and measuring specific bio signals. The guidance information may be provided to a user by using the imaging unit 510 or the speaker 530 of FIG. 5. However, the embodiment is not limited to this, and the guidance information may be provided using various output devices such as braille characters.

In operation S120, the controller 113 sets a bio signal measurement reference and a stimulation provision reference. The controller 113 may set a bio signal measurement reference and a stimulation provision reference based on personal information or personal identification information. In addition, the controller 113 may consider the response signal provided by the user in response to the guidance information to set a bio signal measurement reference and a stimulation provision reference. The degree of response to stimulation, the degree of recognizing stimulation, and the degree of maintaining a stabilization state vary for each individual. The controller 113 may use personal information or personal identification information to determine the intensity of stimulation, the provision duration of stimulation, the type of stimulation, the measurement time point of bio signal, and the type of bio signal. Thus, optimized data for analyzing a user's health function may be extracted.

In operation S130, the bio signal measurement device 112 measures the first bio signal from the stabilized user. The bio signal measurement device 112 measures the first bio signal according to the bio signal measurement reference set by the controller 113. In operation S135, the controller 113 extracts a first feature factor from the first bio signal. The controller 113 may set an extraction reference of a feature factor and a classification reference of a feature factor based on personal information or personal identification information. That is, since user's unique physiological characteristics are considered, the reliability of the extracted first feature factor may be improved.

In operation S140, the stimulation providing device 111 provides stimulation to a user. The stimulation providing device 111 provides stimulation according to the stimulation provision reference set by the controller 113. In operation S150, the bio signal measurement device 112 measures a second bio signal from a user in a perturbation state according to stimulation. The bio signal measurement device 112 measures the second bio signal according to the bio signal measurement reference set by the controller 113. In operation S155, the controller 113 extracts a second feature factor from the second bio signal. The controller 113 may extract the second feature factor according to the set extraction reference of the feature factor and the set classification reference of the feature factor.

In operation S160, the stimulation providing device 111 terminates the stimulation provision to the user. The stimulation providing device 111 terminates the stimulation provision according to the stimulation provision reference set by the controller 113. In operation S170, the bio signal measurement device 112 measures a third bio signal from a user in a restored stabilization state. The bio signal measurement device 112 measures the third bio signal according to the bio signal measurement reference set by the controller 113. In operation S175, the controller 113 extracts a third feature factor from the third bio signal. The controller 113 may extract the third feature factor according to the set extraction reference of the feature factor and the set classification reference of the feature factor.

In operation S180, the health function analysis device 122 of the management server 120 may evaluate and predict a health function. The controller 113 may classify the first to third feature factors by each physiological function. The controller 113 may compare the classified first to third feature factors. The controller 113 may generate physiological function data based on the amount of changes in the first to third feature factors. The controller 113 or the health function analysis device 122 may classify physiological function data. The controller 113 or the health function analysis device 122 may generate health function data by analyzing the classified physiological function data. Physiological function data and health function data may be grouped into one visit data and stored in the data storage unit 121. In addition, bio signal data, stimulation data, and feature factor data may be stored in data storage unit 121 as one visit data together with physiological function data and health function data.

The health function analysis device 122 may compare the visit data stored at the previous visit with the recently stored visit data to evaluate the health function of the user and predict the health function. The health function analysis device 122 may extract the change amount of visit data through comparison between visit data. The health function analysis device 122 may analyze the present absolute health function through recently stored visit data. Further, the health function analysis device 122 may analyze the variation of the relative health function from the extracted change amount. The health function analysis device 122 may predict a future health function from the extracted variation.

In operation S190, the management server 120 generates personal identification information. The health function analysis device 122 may analyze the stored visit data to pattern the health trend of the user. The health function analysis device 120 may generate personal identification information based on the patterned health trend. The health function varies over time. Thus, personal identification information may change continuously. The personal identification information is stored in the data storage unit 121. When the user additionally uses the health data collection device 110, the user may be identified by the personal identification information generated by the management server 120.

Personal identification information may be used not only to identify a user but also as a classification code for the evaluation of a health function. For example, visit data or data related to analyzed health variation are classified over time, and a common factor may be extracted from specific changes inherent to the user. That is, a classification code for evaluation of a health function may be defined through accumulated data classification. A factor of the health function data having the same tendency may be defined as one classification code. When analyzing the health function in the future, the classification and analysis of the user's health function may be performed using the classification code. The classification code may change according to the accumulation of visit data. The classification code may be different for each individual.

Figure 9:
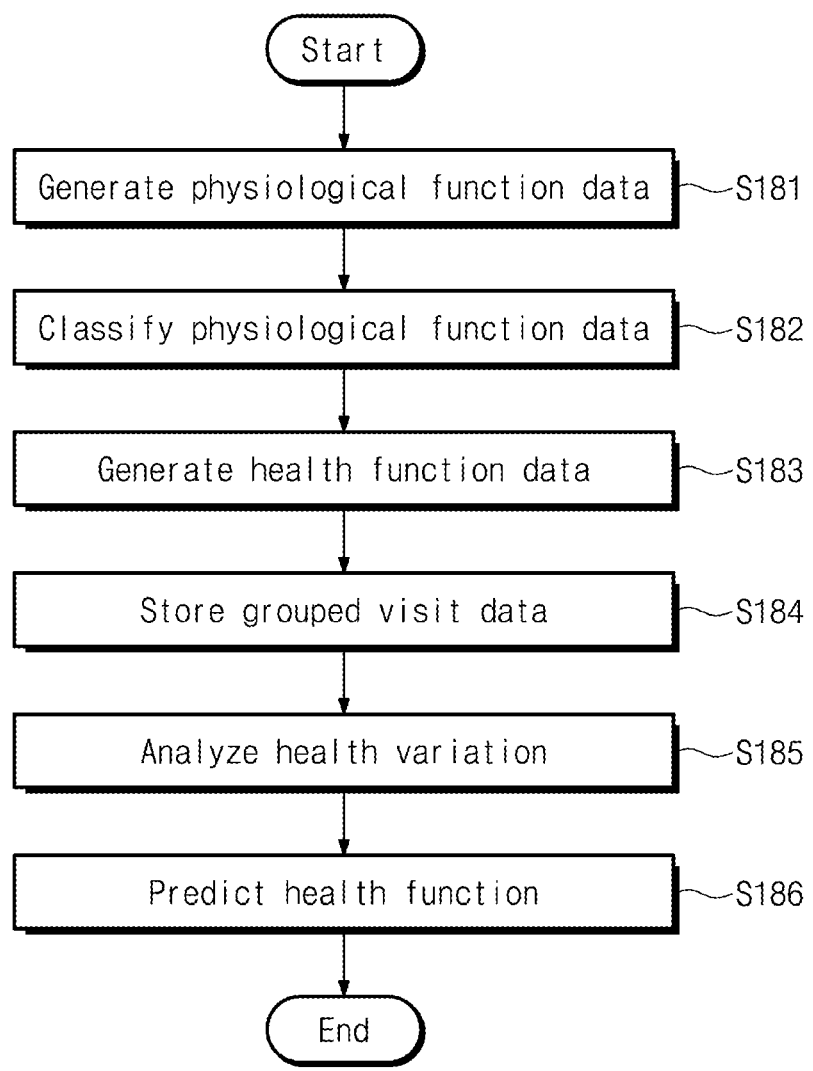
FIG. 9 is a flowchart embodying operation S180 of FIG. 8.

FIG. 9 is a flowchart embodying operation S180 of FIG. 8. The operations of evaluating and predicting a health function may be performed in the health evaluation system 100 of FIG. 1 or the health evaluation system 200 of FIG. 2. Referring to FIG. 9, the operations of evaluating and predicting a health function may be performed in the health data collection device 110 or the health function analysis device 122. Hereinafter, the operations of evaluating and predicting the health function in correspondence to the components of FIG. 1 will be described.

In operation S181, the health data collection device 110 may generate physiological function data. The health data collection device 110 generates physiological function data based on the extracted first to third feature factors. Physiological function data may be data related to the function of each human body organ, that is, the physiological function. Although it is described that operation S181 is performed in the health data collection device 110, physiological function data may be generated in the health function analysis device 122 without limitation.

The health data collection device 110 may classify the first to third feature factors into physiological functions. As a result of measuring various bio signals, each of the first to third feature factors may include a plurality of feature factors. One feature factor may be related to a plurality of physiological functions. In this case, one feature factor may be used to generate a plurality of physiological function data. Some of the plurality of feature factors may be related to the same physiological function. In this case, the corresponding feature factors may be used to generate one physiological function data.

The physiological function data may include first physiological function data in a stabilization state, second physiological function data in a perturbation state, and third physiological function data in a restored stabilization state. The physiological function data includes physiological function change amount data according to a change amount between the first feature factor and the second feature factor, physiological function change amount data according to a change amount between the second feature factor and the third feature factor, and physiological function change amount data according to the change amount between the first feature factor and the third feature factor.

In operation S182, the health data collection device 110 may classify physiological function data. The health data collection device 110 may classify physiological function data using a human body anatomical classification scheme. For example, physiological function data may be categorized based on a correlation of the human body function in the physiological function data and the anatomical system. Although it is described that operation S182 is performed in the health data collection device 110, the physiological function data may be classified in the health function analysis device 122 without limitation.

In operation S183, the health function analysis device 122 may generate health function data. The health function analysis device 122 may generate health function data based on the classified physiological function data. The health function data may be data related to an index for evaluating a user's health state. Although it is described that operation S183 is performed in the health function analysis device 122, the health function data may be generated in the health data collection device 110 without limitation.

The health function data may include first health function data in a stabilization state, second health function data in a perturbation state, and third health function data in a recovered stabilization state. The first to third health function data may represent a health state in the corresponding state. In addition, the health function data may include the integrated health function data extracted from the change of the first to third health function data. The integrated health function data may represent a health state at the time of using the health data collection device 110.

In operation S184, visit data is stored in the data storage unit 121 of the management server 120. Bio signal data, stimulation data, feature factor data, physiological function data, and health function data may be grouped into one visit data and stored in the data storage unit 121. A plurality of visit data may be stored in the data storage unit 121 according to the number of times of using the health data collection device 110. The average data and the standard deviation data of the health function data included in each of the plurality of visit data may be additionally stored in the data storage unit 121.

In operation S185, the health function analysis device 122 may analyze the health variation of the user. The health function analysis device 122 may calculate the storage time point of each of the plurality of visit data. The health function analysis device 122 compares the currently provided visit data with the previously stored visit data to extract the change amount. For example, the health function analysis device 122 may analyze a temporal change amount of physiological function data or health function data included in the visit data. If there are a plurality of previously stored visit data, the health function analysis device 122 may compare each of the previously stored visit data with the currently provided visit data. The health function analysis device 122 may generate health variation data related to a user's health variation.

In operation S186, the health function analysis device 122 may predict the health function of the user. The health function analysis device 122 may analyze health variations to predict changes in health function at a specific time point. For example, the health function analysis device 122 may analyze a health variation to calculate a pattern of a user's health function. The health function analysis device 122 may predict future health functions based on the pattern of the calculated health function. The health function analysis device 122 may generate health function prediction data related to the prediction of the user's health function.

Figure 10:
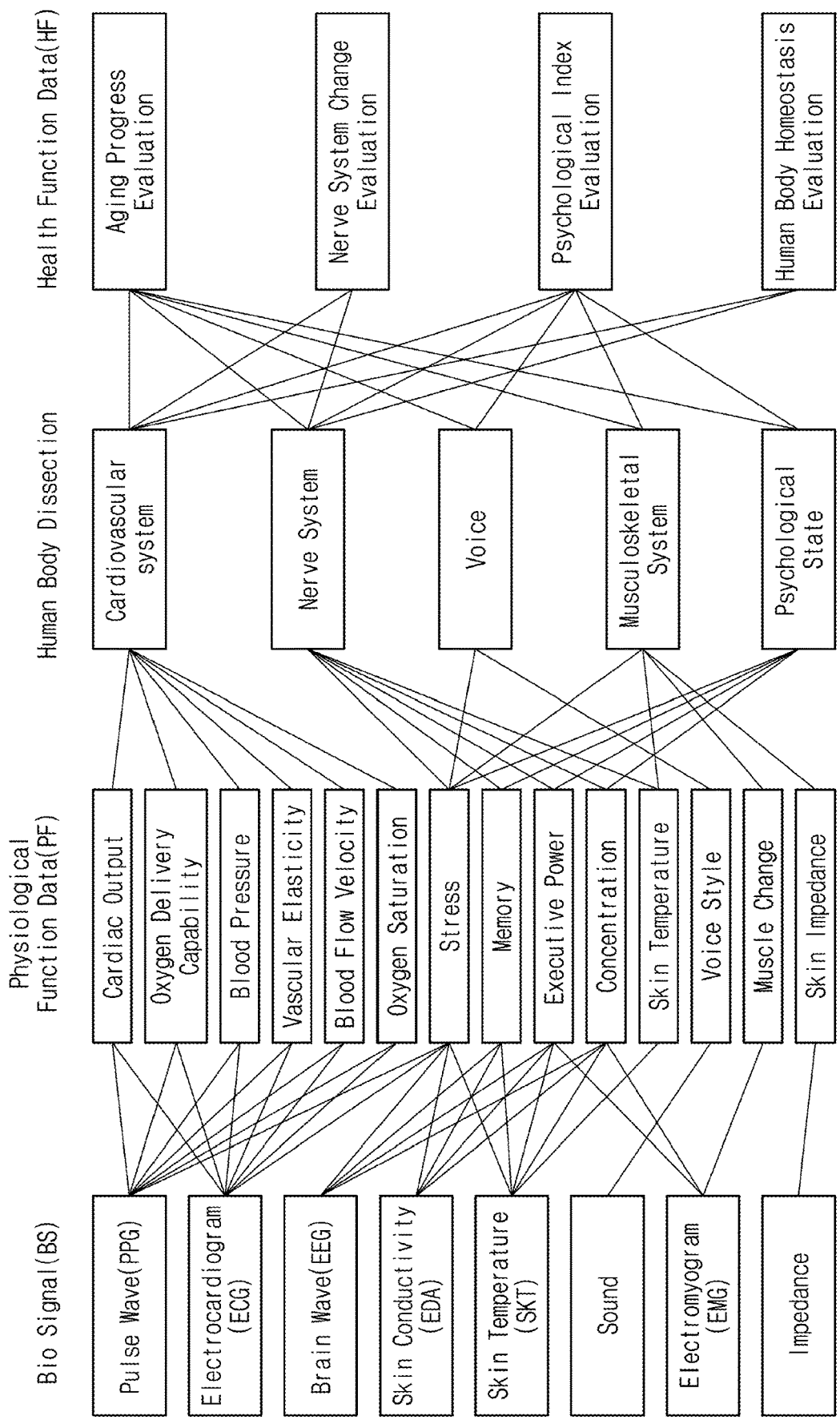
FIG. 10 is a view for explaining the association of bio signal, physiological function data, and health function data.

FIG. 10 is a view for explaining the association of bio signal, physiological function data, and health function data. Referring to FIG. 10, the relationship between bio signal BS and physiological function data PF is shown. The relationship between the physiological function data PF and the health function data HF is shown through the human body anatomical classification method. It will be understood that the association of FIG. 10 is an example. Therefore, in the process of generating the physiological function data or the health function data of the inventive concept's health evaluation system or health data collection device, a relationship different from FIG. 10 may be shown. In addition, physiological function data or health function data may also be generated from association relationships added or deleted in FIG. 10.

The bio signal BS may include bio signals related to pulse waves (PPG), electrocardiogram (ECG), electroencephalogram (EEG), skin conductivity (EDA), skin temperature (SKT), sound, electromyogram (EMG), and impedance. Each of the feature factors extracted from bio signals may represent the characteristics of these bio signals. Each of the bio signals may be related to at least one physiological function data PF. The physiological function data PF is related to cardiac output, oxygen delivery capability, blood pressure, blood vessel elasticity, blood flow velocity, oxygen saturation, stress, memory, executive power, concentration, skin temperature, voice style, muscle change, and skin impedance. The measured pulse wave (PPG) may be used to extract physiological function data on cardiac output, oxygen delivery capability, blood pressure, vascular elasticity, blood flow velocity, oxygen saturation, and stress index. The measured electrocardiogram (ECG) may be used to extract physiological function data on cardiac output, oxygen delivery capability, blood pressure, vascular elasticity, blood flow velocity, oxygen saturation, and stress index. The measured electroencephalogram (EEG) may be used to extract physiological function data on stress index, memory, executive power, and concentration. The measured skin conductivity (EDA) may be used to extract physiological function data on stress index, memory, executive power, and concentration.

The measured skin temperature (SKT) may be used to extract physiological function data on stress index, memory, executive power, and concentration, and skin temperature. The measured sound may be used to extract physiological function data on voice style, i.e., changes in voice print. The measured electromyogram (EMG) may be used to extract physiological function data on executive power, concentration, and changes in muscle. The measured impedance may be used to extract physiological function data on skin dryness or aging due to changes in skin impedance.

The physiological function data PF may be classified according to a human body anatomical classification method. The Physiological function data PF may be classified into cardiovascular system, nerve system, vocal, musculoskeletal system, and psychological state. The physiological function data on cardiac output, oxygen delivery capability, blood pressure, vascular elasticity, blood flow velocity, and oxygen saturation may be classified as physiological function data related to a cardiovascular system. The physiological function data on stress index, memory, executive power, concentration, and skin temperature may be classified as physiological function data related to a nerve system. The physiological function data on stress index and voice style may be classified as physiological function data related to voice. The physiological function data on stress index, skin temperature, changes in muscle, and changes in skin impedance may be classified as physiological function data related to a musculoskeletal system. The physiological function data on stress index, memory, executive power, and concentration may be classified as physiological function data related to psychological state.

The classified physiological function data may be related to at least one health function data HF. The health function data HF may include health function data on aging progress, changes in nerve system, psychological index, and changes in human body homeostasis. Health function data on aging progress may be generated using physiological function data related to cardiovascular system, nerve system, vocal, musculoskeletal system, and psychological state. Health function data on changes in nerve system may be generated using physiological function data related to cardiovascular and nerve systems. Health function data on physiological index may be generated using physiological function data related to cardiovascular system, nerve system, vocal, musculoskeletal system, and psychological state. Health function data on human body homeostasis may be generated using physiological function data related to cardiovascular and nerve systems.

Figure 11:
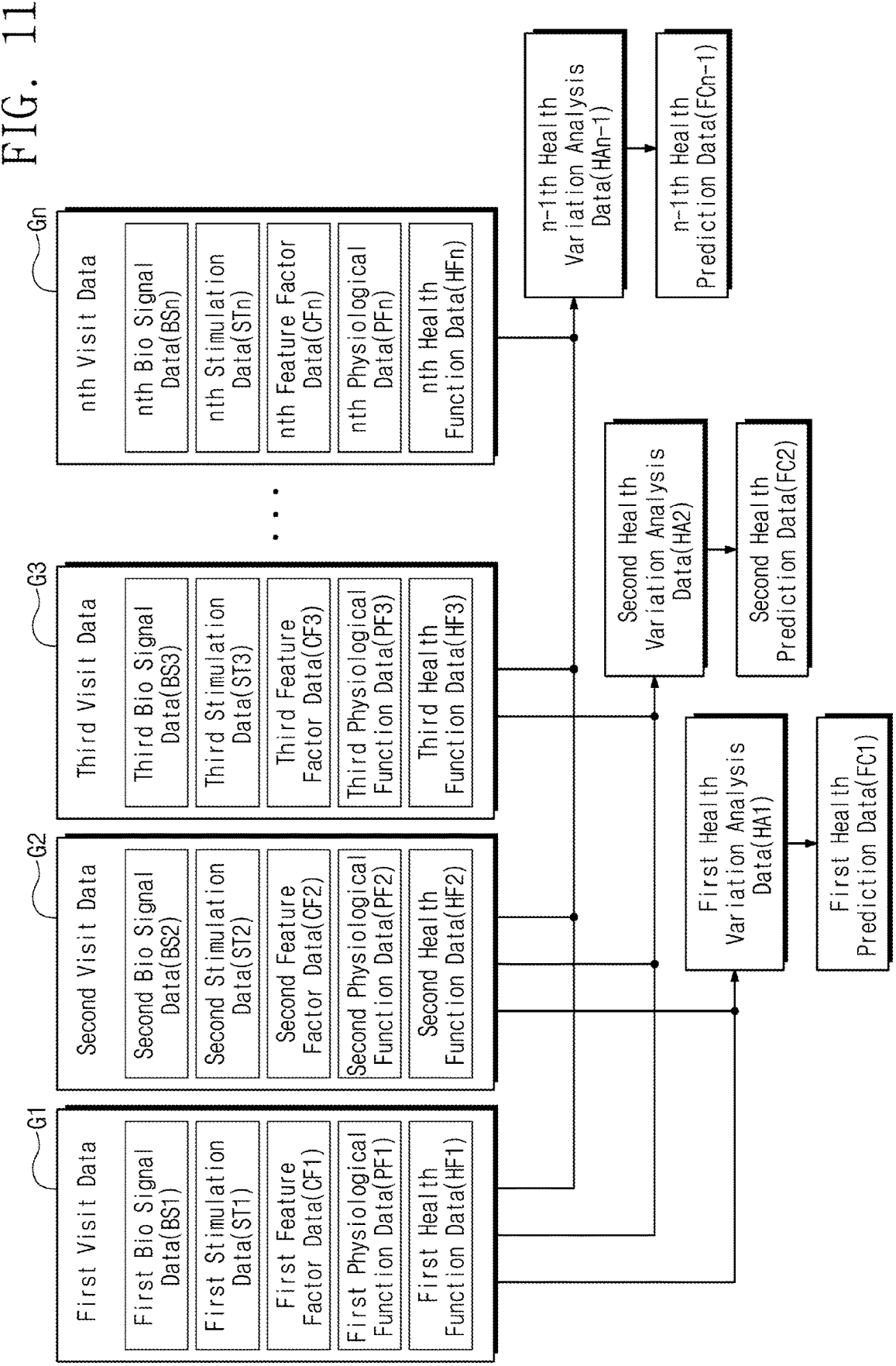
FIG. 11 is a view for explaining a process of analyzing and predicting a health variation.

FIG. 11 is a view for explaining a process of analyzing and predicting a health variation. Referring to FIG. 11, first to nth visit data G1 to Gn are generated. The first to nth visit data G1 to Gn are stored in the data storage unit 121 of FIG. 1. It is assumed that a user uses a health data collection device n times over time. Each of the first to nth visit data G1 to Gn includes bio signal data BS1 to BSn, stimulation data ST1 to STn, feature factor data CF1 to CFn, physiological function data PF1 to PFn, and health function data HF1 to HFn. Hereinafter, FIG. 11 will be described in correspondence to the components of FIG. 1.

When the user firstly uses the health data collection device 110, the first visit data G1 is stored in the management server 120. When the user secondly uses the health data collection device 110, the second visit data G2 is stored in the management server 120. The health function analysis device 122 may calculate the time between the time point at which the first visit data G1 is stored and the time point at which the second visit data G2 is stored. The health function analysis device 122 may calculate a change amount between the first visit data G1 and the second visit data G2 according to the calculated time. For example, the first physiological function data PF1 and the second physiological function data PF2 may be compared, or the first health function data HF1 and the second health function data HF2 may be compared.

The health function analysis device 122 may generate first health variation analysis data HA1 based on the change amount between the visit data G1 and the second visit data G2. The health function analysis device 122 may calculate the pattern of the health function using the first health variation analysis data HA1. The health function analysis device 122 may calculate a future health variation degree or a health function change amount from the calculated pattern. The health function analysis device 122 may generate first health prediction data FC1 based on the calculated pattern.

Similar to the above description, when the user uses the third health data collection device 110, the third visit data G3 is stored in the management server 120. The health function analysis device 122 may calculate the change amount between the first visit data G1 and the third visit data G3 and between the second visit data G2 and the third visit data G3. The health function analysis device 122 may generate the second health variation analysis data HA2 based on the change amount of the first to third visit data G1 to G3. The health function analysis device 122 may generate the second health prediction data FC2 based on the second health variation analysis data HA2.

Unlike FIG. 11, the second health variation analysis data HA2 or the second health prediction data FC2 may not be generated using all of the first to third visit data G1 to G3. For example, the second health variation analysis data HA2 may be generated based on the change amounts of the second visit data G2 and the third visit data G3, and the first health variation analysis data HA1.

By using the first to third visit data G1 to G3, an error of each visit data may be detected. For example, the management server 120 compares the first visit data G1 with the third visit data G3 and compares the second visit data G2 with the third visit data G3 to detect an error of the visit data G2 or the third visit data G3. The management server 120 may calculate the error range and error rate of the visit data using a linear or non-linear method. Similarly, when the nth visit data Gn is stored, the management server 120 may compare the nth visit data Gn with each of the first to n−1th visit data G1 to Gn−1 to calculate the error range and error rate of the visit data. The error of the visit data may be continuously detected as the number of times of using the health data collection device 110 is increased. Thus, the accuracy of health variation analysis data and health prediction data may be increased. The error range or error rate may be stored in the data storage unit 121 together with information on the number of times of using the health data collection device 110.

The health function analysis device 122 may detect a section in which the change of visit data is abruptly changed. Thus, the time point at which health deteriorates may be accurately and easily predicted. The health function analysis device 122 may analyze changes in visit data to detect a time point at which a singular point occurs or a time point at which an inflection point is formed to detect a disease occurrence time point. Since the health function analysis device 122 uses various physiological function data, the cause of the disease occurrence may be identified. The health function analysis device 122 may calculate a period in which the health function changes. The health function analysis device 122 may generate an individual disease occurrence progression pattern based on the calculated period and generate health prediction data.

The personal identification information may also be used as an index for predicting a health function by itself. Like the health variation analysis data and the health prediction data, as the visit data accumulates, the personal identification information continuously changes. That is, personal identification information may have a unique pattern that reflects complex bio signals, changes in bio signals for stimulation, and feature factors extracted from changing bio signals. The unique feature pattern of personal identification information may reflect an individual's illness or disease, and the feature pattern itself may represent an individual's constitution.

Figure 12:
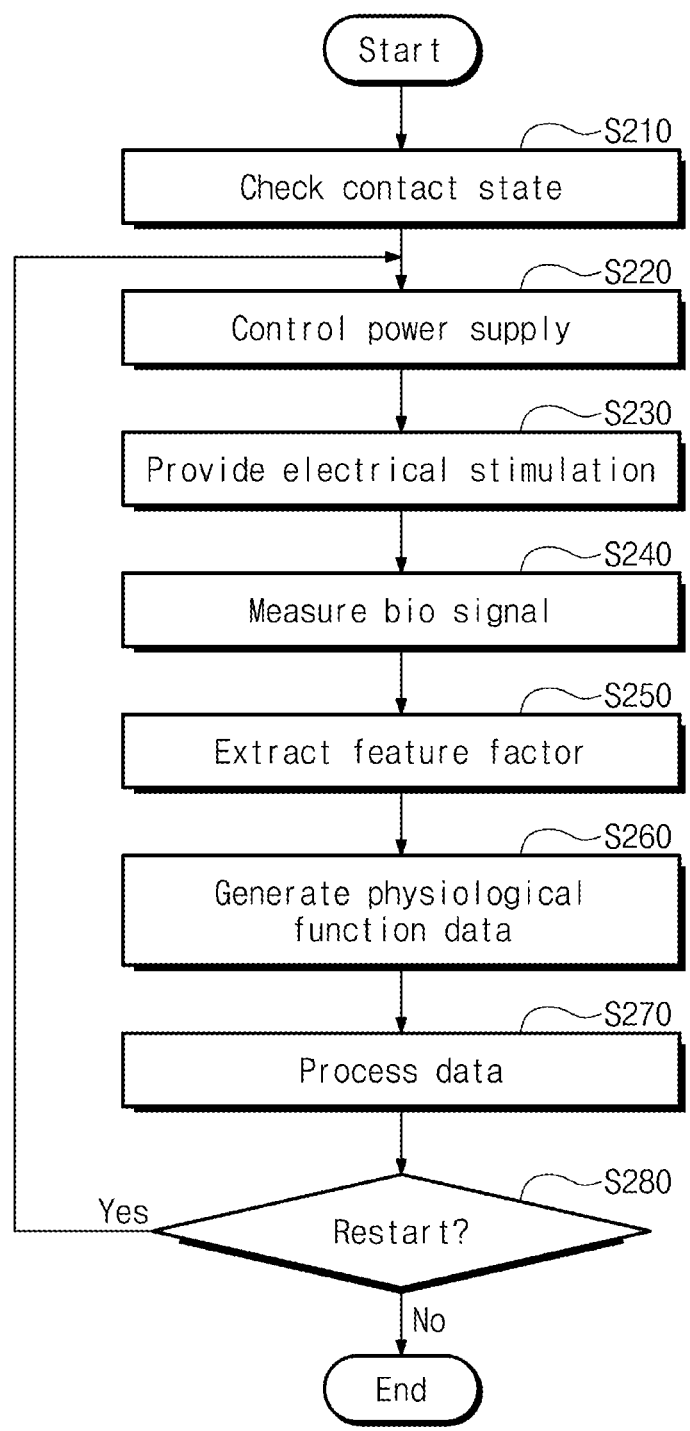
FIG. 12 is a flowchart for explaining a process of collecting and processing data when providing electrical stimulation.

FIG. 12 is a flowchart for explaining a process of collecting and processing data when providing electrical stimulation. The process of FIG. 12 may be performed in the health evaluation system 100 of FIG. 1 or the health evaluation system 200 of FIG. 2. Also, some operations shown in FIG. 12 may be performed in any one of the health data collection devices 300 to 700 of FIGS. 3 to 7. Hereinafter, the process of FIG. 12 will be described in correspondence to the components of FIG. 1.

In operation S210, the health data collection device 110 confirms the contact state. When the health data collection device 110 provides stimulation and measures bio signals, the contact state between a user and the health data collection device 110 may determine the reliability of the physiological function data and the health function data. The health data collection device 110 may measure the resistance between the contact terminals to determine the contact state between the user and the health data collection device 110. If the measured resistance is lower than the reference resistance, it is determined that the contact state between the user and the health data collection device 110 is normal. In this case, operation S220 is performed. If the measured resistance is not lower than the reference resistance, it is determined that the contact state between the user and the health data collection device 110 is abnormal. In this case, the health data collection device 110 may provide information to the user to guide the contact with the health data collection device 110.

In operation S220, the power supply of the health data collection device 110 is controlled. The power supply means the power required to provide electrical stimulation to the user. The supply of power may be started by providing a low power. The power source may be provided in alternating current or direct current. The power supply may be controlled based on personal information or personal identification information. The limit of electrical stimulation and the degree of detecting electrical stimulation are different from person to person. For example, a sensitive user may show a high response at low current, and a dull user may hardly react to the same current. The health data collection device 110 sets a reference to a user's sensation based on personal information or personal identification information.

In operation S230, the stimulation providing device 111 provides electrical stimulation to a user. The stimulation providing device 111 may provide electrical stimulation based on personal information or personal identification information. Electrical stimulation is transmitted to the brain, i.e., the central nerve system, through the sensory nerves of the user. This causes a variation in the central nerve system and peripheral nerve system of the user.

In operation S240, the bio signal measurement device 112 measures the bio signal. The bio signal measurement device 112 may measure the bio signal based on personal information or personal identification information. The bio signal measurement device 112 measures a first bio signal before providing electrical stimulation. The bio signal measurement device 112 measures a second bio signal while providing electrical stimulation. The bio signal measurement device 112 measures a third bio signal after providing electrical stimulation. The bio signal may include at least one of bio signals on electrocardiogram, pulse wave, skin conductivity, skin temperature, and brain wave.

In operation S250, the controller 113 extracts a feature factor from the measured bio signal. The controller 113 may extract feature factors for electrocardiogram, pulse wave, skin conductivity, skin temperature, and brain wave from the bio signal. In operation S260, the controller 113 generates physiological function data. The controller 113 may extract physiological functions for a feature factor responding to electrical stimulation to generate physiological function data.

In operation S270, the controller 113 processes the generated data. The generated data may include bio signal data obtained by converting the measured bio signal, stimulation data that includes information about electrical stimulation, feature factor data, and physiological function data. The controller 113 classifies the generated data. The health data collection device 110 may transmit data generated using the communication device to the management server 120. The transmitted data is stored in the data storage unit 121 as visit data.

In operation S280, the health data collection device 110 may determine whether to restart when the transmitted data is stored. If the restart is determined, operation S220 is performed. In this case, the health data collection device 110 may set the electrical stimulation to be higher or lower than the electrical stimulation previously provided. The restart is determined to analyze changes in bio signal or physiological function data according to changes in electrical stimulation intensity. Operations S220 to S280 are repeated, but if the intensity of the electrical stimulation is changed, a relationship between the physiological function data and the current may appear. However, if no restart is required, the process is terminated.

After the entire process is terminated, the management server 120 may analyze the stored visit data. The management server 120 may compare the previous visit data with the currently stored visit data to analyze the health variation of the user and predict the health state. Also, the management server 120 may generate personal identification information using the visit data. For example, the management server 120 may pattern a feature factor for electrical stimulation having a specific current value and pattern a feature factor for electrical stimulation having a current value that is higher or lower than a specific current value. The management server 120 may implement an association of the patterned feature factor and current as a shaped pattern. The feature of the shaped pattern may be used as personal identification information.

Figure 13:
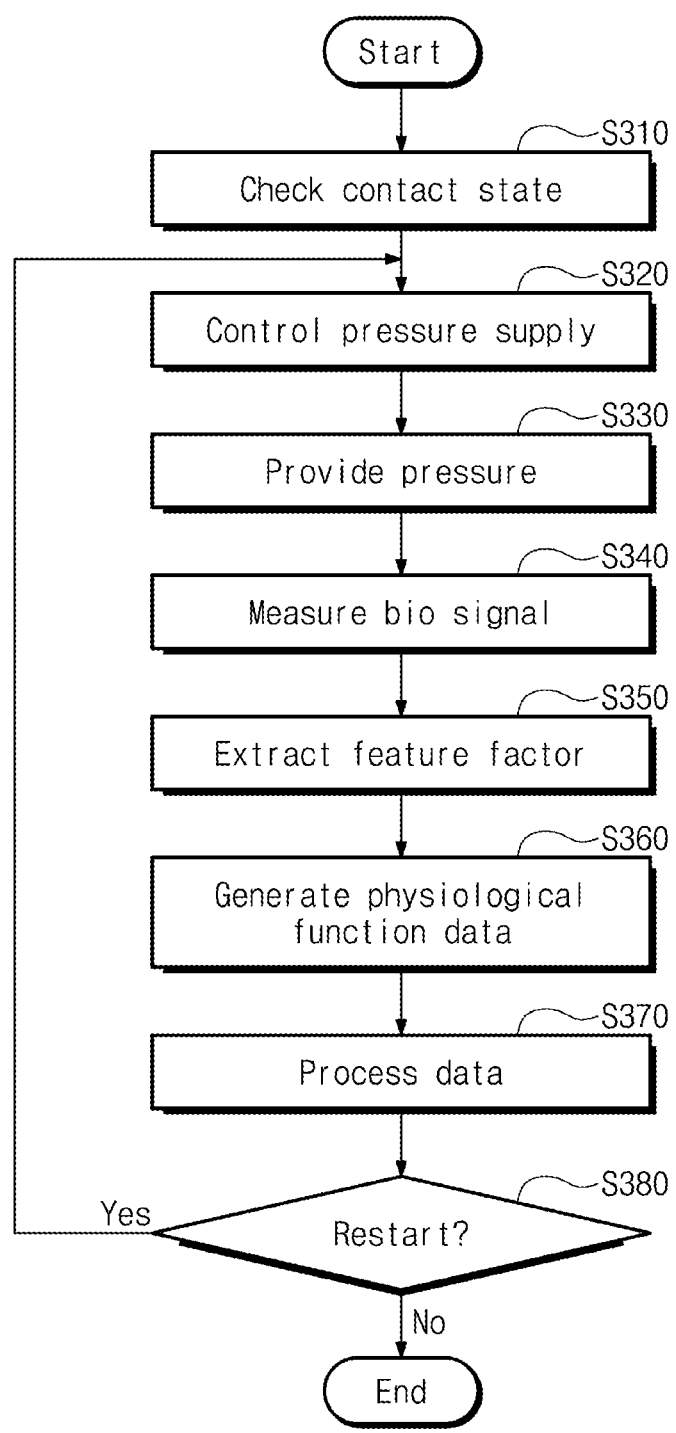
FIG. 13 is a flowchart for explaining a process of collecting and processing data when providing pressure stimulation.

FIG. 13 is a flowchart for explaining a process of collecting and processing data when providing pressure stimulation. The process of FIG. 13 may be performed in the health evaluation system 100 of FIG. 1 or the health evaluation system 200 of FIG. 2. Also, some operations shown in FIG. 13 may be performed in any one of the health data collection devices 300 to 700 of FIGS. 3 to 7. Hereinafter, the process of FIG. 13 will be described in correspondence to the components of FIG. 1.

In operation S310, the health data collection device 110 confirms the contact state. When the health data collection device 110 provides stimulation and measures bio signals, the contact state between a user and the health data collection device 110 may determine the reliability of the physiological function data and the health function data. As in operation S210, the health data collection device 110 may measure the resistance between the contact terminals to determine the contact state between the user and the health data collection device 110.

In operation S320, the pressure supply of the health data collection device 110 is controlled. The supply of pressure may be started by providing a low pressure. The pressure supply may be controlled based on personal information or personal identification information. Pressure may provide fine pain. The limit of pressure stimulation and the degree of detecting pressure stimulation are different from person to person. The health data collection device 110 sets a reference to a user's sensation based on personal information or personal identification information.

In operation S330, the stimulation providing device 111 provides pressure to a user. The stimulation providing device 111 may provide pressure stimulation based on personal information or personal identification information. The pressure may not be maintained constantly, but may be provided in the form of a pulse. That is, the stimulation providing device 111 may provide pressure and repeat a pressure removal state. When a pressure above the threshold is provided to a pain spot where a user feels pain, the user senses the pain. Depending on the pain, the activity of the central nerve system changes, and the central nerve system and the peripheral nervous system are changed.

In operation S340, the bio signal measurement device 112 measures the bio signal. The bio signal measurement device 112 may measure the bio signal based on personal information or personal identification information. The bio signal measurement device 112 measures a first bio signal before providing pressure stimulation. The bio signal measurement device 112 measures a second bio signal while providing pressure stimulation. The bio signal measurement device 112 measures a third bio signal after providing pressure stimulation. The bio signal may include at least one of bio signals on electrocardiogram, pulse wave, skin conductivity, skin temperature, and brain wave.

In operation S350, the controller 113 extracts a feature factor from the measured bio signal. The controller 113 may extract feature factors for electrocardiogram, pulse wave, skin conductivity, skin temperature, and brain wave from the bio signal. In operation S360, the controller 113 generates physiological function data. The controller 113 may extract physiological functions for a feature factor responding to pressure stimulation to generate physiological function data.

In operation S370, the controller 113 processes the generated data. The generated data may include bio signal data obtained by converting the measured bio signal, stimulation data that includes information about pressure stimulation, feature factor data, and physiological function data. The controller 113 classifies the generated data. The health data collection device 110 may transmit data generated using the communication device to the management server 120. The transmitted data is stored in the data storage unit 121 as visit data.

In operation S380, the health data collection device 110 may determine whether to restart when the transmitted data is stored. If the restart is determined, operation S320 is performed. In this case, the health data collection device 110 may set the pressure stimulation to be higher or lower than the pressure stimulation previously provided. The restart is determined to analyze changes in bio signal or physiological function data according to changes in pressure stimulation intensity. Operations S220 to S280 are repeated, but if the intensity of the pressure stimulation is changed, a relationship between the physiological function data and the pressure may appear. However, if no restart is required, the process is terminated.

After the entire process is terminated, the management server 120 may analyze the stored visit data. The management server 120 may assume the pressure changes before and after providing stimulation as one dimension and assume the signals of the changing peripheral and central nerve systems as a plurality of dimensions. The management server 120 may analyze changes in the nerve system as the pressure changes. Also, even though the same pressure is provided before and after stimulation, the pain felt by the user based on the adaptation of the central nerve system is different. These changes in pain vary from person to person. The management server 120 may evaluate and predict the health state by analyzing pain changes, pain adaptation, or habituation.

The management server 120 may compare the previous visit data with the currently stored visit data to analyze the health variation of the user and predict the health state. Also, the management server 120 may generate personal identification information using the visit data. For example, the management server 120 may pattern the feature factor for a specific pressure stimulation that causes pain and pattern a pain change or a pain adaptation degree with respect to a pressure above or below a specific pressure. The patterned pain change or pain adaptation degree may be used as personal identification information.

Figure 14:
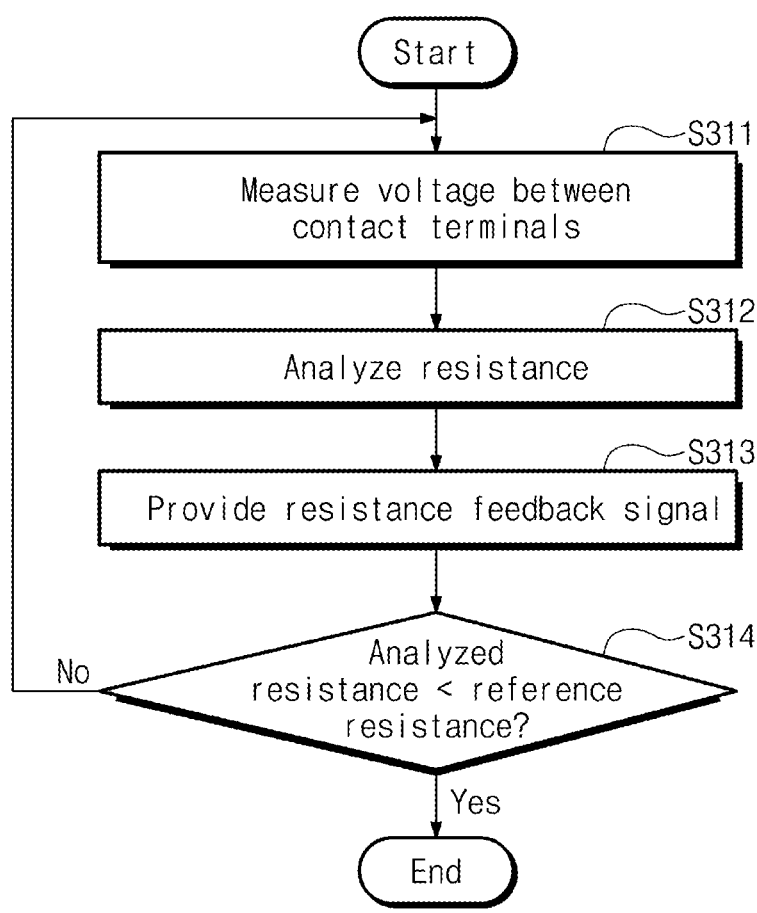
FIG. 14 is a flowchart embodying operation S210 of FIG. 12 or operation S310 of FIG. 13.

FIG. 14 is a flowchart embodying operation S210 of FIG. 12 or operation S310 of FIG. 13. Hereinafter, an operation of confirming a contact state corresponding to the components of FIG. 1 will be described. In operation S311, the health data collection device 110 measures the voltage between the contact terminals. Power is supplied to the contact terminals, and the voltage between the contact terminals is measured. In operation S312, the health data collection device 110 measures the resistance between the contact terminals. Based on the measured voltage, the resistance between the contact terminals may be analyzed. For example, in addition to the measured voltage, the health data collection device 110 may measure the current to analyze the resistance. In operation S313, the health data collection device 110 generates a resistance feedback signal. The health data collection device 110 may recognize a resistance value between the contact terminals by the resistance feedback signal.

In operation S314, the health data collection device 110 compares the analyzed resistance with the reference resistance. When the user and the contact terminals are in contact, the analyzed resistance has a lower resistance value than a reference resistance. If the user and the contact terminals are not normally contacted, the analyzed resistance has a higher resistance value than the reference resistance. Accordingly, if the analyzed resistance is lower than the reference resistance, the health data collection device 110 determines that the contact state is normal. In this case, operation S220 of FIG. 12 or operation S320 of FIG. 13 may be performed. If the analyzed resistance is not lower than the reference resistance, the health data collection device 110 determines that the contact state is bad. In this case, operation S311 is performed. That is, the operation of confirming the contact state is repeated until the contact state between the user and the contact terminals is normal.

Figure 15:
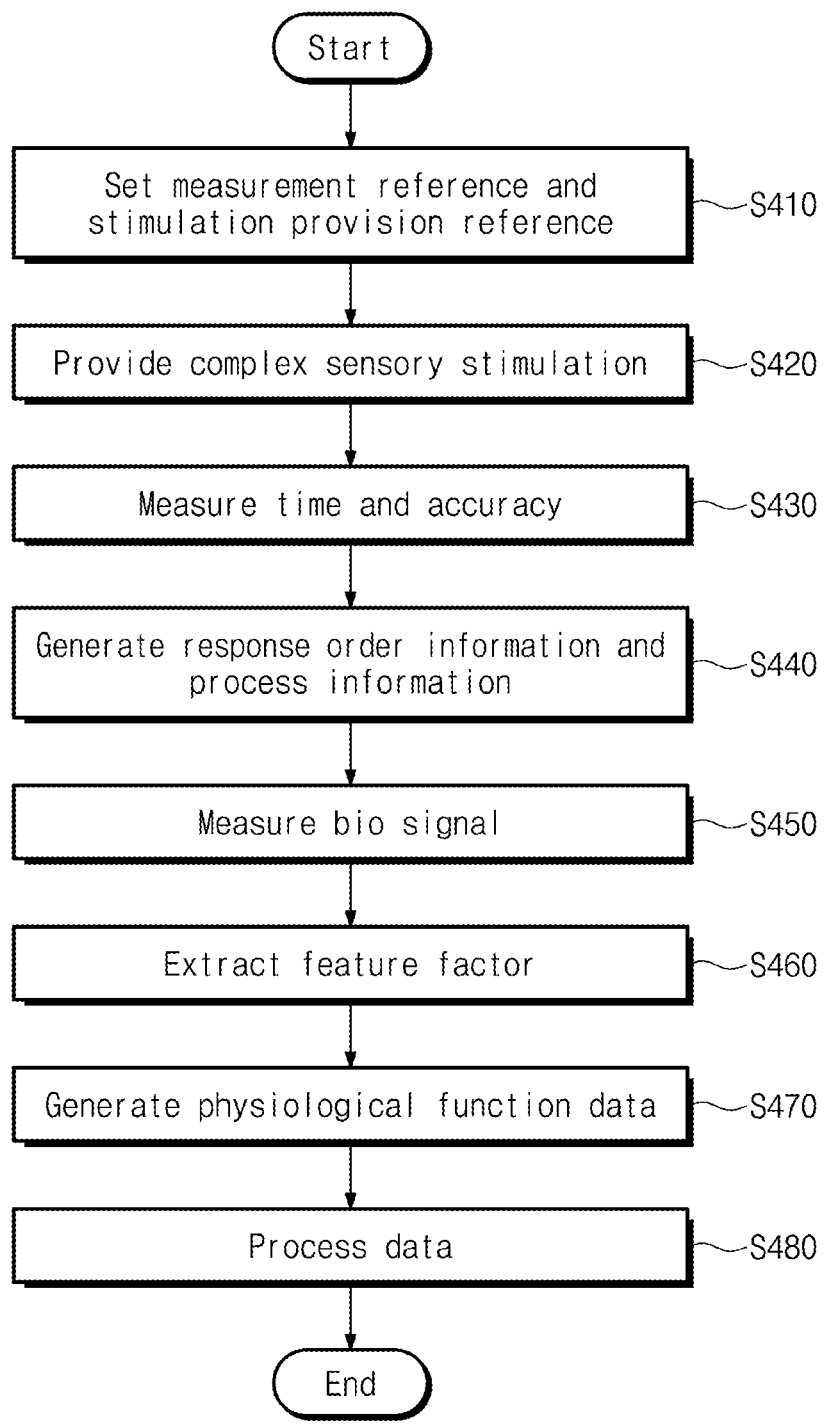
FIG. 15 is a view for explaining a process of collecting and processing data when providing complex sensory stimulations.

FIG. 15 is a view for explaining a process of collecting and processing data when providing complex sensory stimulations. Complex sensory stimulations may mean providing a user with at least two stimulations of visual, auditory, tactile, olfactory, and taste related stimulations. The process of FIG. 15 will be understood as one embodiment, and the process of collecting and processing data when providing complex sensory stimulations is not limited to FIG. 15. The process of FIG. 15 may be performed in the health evaluation system 100 of FIG. 1 or the health evaluation system 200 of FIG. 2. Also, some operations shown in FIG. 15 may be performed in any one of the health data collection devices 300 to 700 of FIGS. 3 to 7. Hereinafter, the process of FIG. 15 will be described in correspondence to the components of FIG. 1.

In operation S410, the health data collection device 110 sets a bio signal measurement reference and a reference for providing stimulation to the user. The health data collection device 110 sets the bio signal measurement reference and the reference for providing stimulation to the user based on personal information or personal identification information. The health data collection device 110 may determine the type of sensation to be provided to the user, the intensity of sensation, and the time point of providing sensation based on the personal information or the personal identification information. In addition, the health data collection device 110 may determine the number of times of providing complex sensory stimulations.

In operation S420, the stimulation providing device 111 provides the user with complex sensory stimulations. The stimulation providing device 111 may provide complex sensory stimulations according to a reference set based on personal information or personal identification information. For example, two or more sensory stimulations may be selected from visual stimulation, auditory stimulation, tactile stimulation, olfactory stimulation, and taste stimulation, depending on the reference for providing stimulation. The stimulation providing device 111 may provide each of the complex sensory stimulations sequentially or simultaneously. In addition, the stimulation providing device 111 may provide complex sensory stimulations several times. The order in which sensory stimulations are presented may be different each time.

In operation S430, the health data collection device 110 measures a user's response time and accuracy with respect to stimulation. If complex sensory stimulations are provided in order, the time to respond to each of sensory stimulations provided in order may be measured. Based on the measured response time, the speed of perceiving stimulation in the central nerve system may be calculated and the nerve response speed may be calculated. When complex sensory stimulations are provided in the form of instructions, the time of performing the process according to complex sensory stimulations and the accuracy of the performance results may be measured. For example, when the stimulation providing device 111 provides a visual instruction and an auditory instruction, the time at which the user performs the instruction using a touch or a voice may be measured. In addition, the accuracy of the user's performance results may be measured.

The response to stimulation may be complex. For example, when visual stimulation and auditory stimulation are provided to a user, the measured response may be a tactile response such as touch movement and an auditory response such as voice. That is, the health data collection device 110 may measure complex sensory responses with respect to complex sensory stimulation. For example, a display included in the health data collection device 110 may display a moving point and a speaker may provide a specific sound. A user may move a touch pen or a laser point to follow a moving point and speak in response to a specific sound. The health data collection device 110 may measure each response time and measure the accuracy of the response.

The response to stimulation may include many errors. Thus, the health data collection device 110 may provide complex sensory stimulations several times and measure the responses to it several times. The average and standard deviation of the response times and accuracies measured the set number of times may be calculated. The reliability range may be set based on the average and the standard deviation. A response time and an accuracy out of the reliability range among the measured response times and accuracies may be determined as errors and eliminated. That is, the reliability of response related information may be improved.

In operation S440, the health data collection device 110 may generate response order information and process information. The response order information may indicate information about the order in which a user responds to each of the sensory stimulations. The process information may indicate information about the entire process performed by the user in accordance with sensory stimulations. The response order information and the process information may be generated based on the measured response time and accuracy of the user.

In operation S450, the bio signal measurement device 112 measures the bio signal. The response to stimulation differs from the bio signal in that it is the intended behavioral pattern for sensory stimulations. The bio signal may be measured with the progress of operations S420 to S440. The bio signal measurement device 112 may measure the bio signal based on personal information or personal identification information. The bio signal measurement device 112 measures a first bio signal before providing complex sensory stimulations. The bio signal measurement device 112 measures a second bio signal while providing complex sensory stimulations. The bio signal measurement device 112 measures a third bio signal after providing complex sensory stimulations.

In operation S460, the controller 113 extracts a feature factor from the measured bio signal. In operation S470, the controller 113 generates physiological function data. The controller 113 may extract physiological functions for a feature factor responding to complex sensory stimulations to generate physiological function data. For example, the controller 113 may generate physiological function data related to a nerve response from a feature factor.

In operation S480, the controller 113 processes the generated data. The generated data may include bio signal data obtained by converting the measured bio signal, stimulation data that includes information about electrical stimulation, feature factor data, and physiological function data. In addition, the generated data may additionally include use response related data, such as response time information, accuracy information, response order information, and process information, which are generated by operations S430 and S440. The controller 113 classifies the generated data. The health data collection device 110 may transmit data generated using the communication device to the management server 120. The transmitted data is stored in the data storage unit 121 as visit data.

Unlike single stimulation, complex nerve responses may be analyzed when providing complex sensory stimulations. In addition, data related to responses by complex sensory stimulations may also be used to analyze the complexity of the central nerve system. That is, the part of the sensory perception that appears in the brain differs depending on the type of sensation. Thus, complex brain functions and variations in complex central nerve systems may be analyzed. For example, the health function analysis device 122 may analyze response patterns corresponding to complex sensory stimulations to evaluate and predict the presence or absence of mental illness such as dementia. The health function analysis device 122 may analyze the response pattern to evaluate and predict aging, which is a factor that lowers the nerve response speed.

After the entire process is terminated, the management server 120 may analyze the stored visit data. The management server 120 may compare the previous visit data with the currently stored visit data to analyze the health variation of the user and predict the health state. Also, the management server 120 may generate personal identification information using the visit data.

Figure 16:
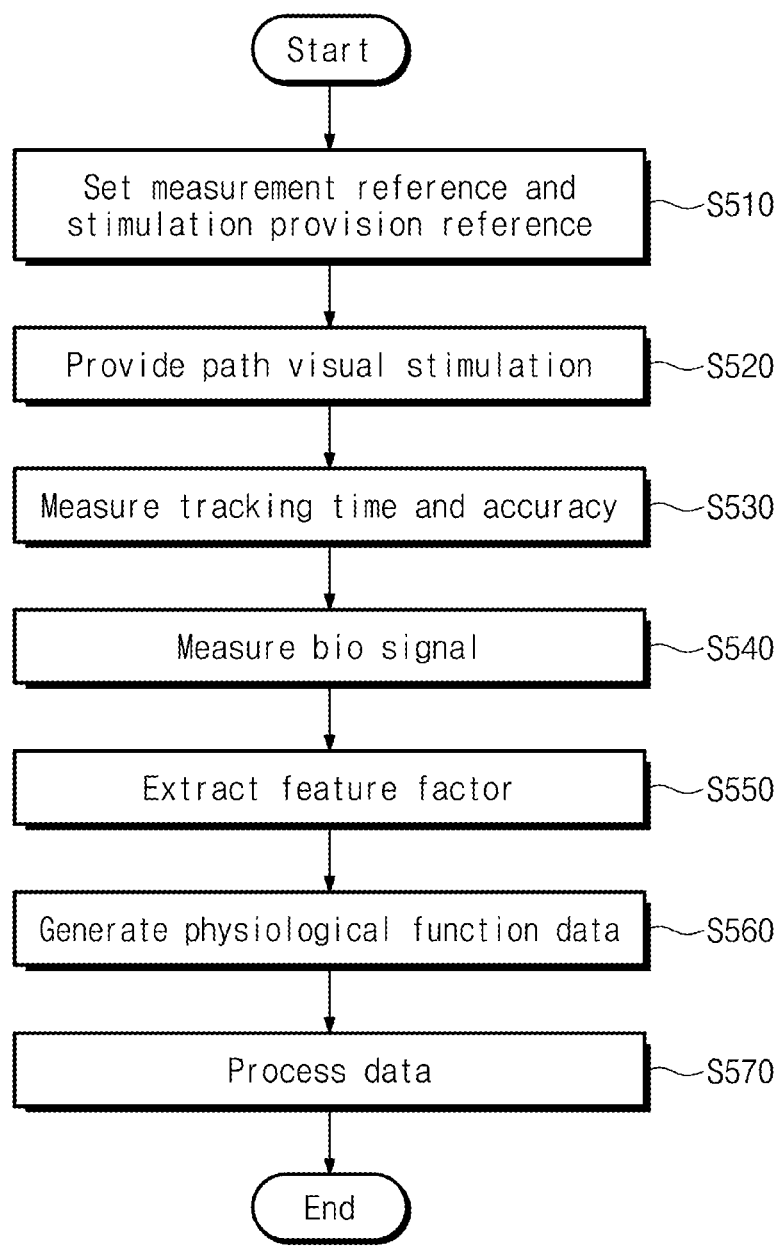
FIG. 16 is a view for explaining a process of collecting and processing data when providing visual stimulation for a path.

FIG. 16 is a view for explaining a process of collecting and processing data when providing visual stimulation for a path. The process of FIG. 16 will be understood as one embodiment, and the process of collecting and processing data when providing stimulation for a path is not limited to FIG. 17. The process of FIG. 16 may be performed in the health evaluation system 100 of FIG. 1 or the health evaluation system 200 of FIG. 2. Also, some operations shown in FIG. 16 may be performed in any one of the health data collection devices 300 to 700 of FIGS. 3 to 7. Hereinafter, the process of FIG. 16 will be described in correspondence to the components of FIG. 1.

In operation S510, the health data collection device 110 sets a bio signal measurement reference and a reference for providing stimulation to the user. The health data collection device 110 sets the bio signal measurement reference and the reference for providing stimulation to the user based on personal information or personal identification information. The health data collection device 110 may determine the type of a path to be provided to the user, and the time point and time of providing visual stimulation based on the personal information or the personal identification information. In addition, the health data collection device 110 may determine the number of times of providing path visual stimulation.

In operation S520, the stimulation providing device 111 provides path visual stimulation to a user. The stimulation providing device 111 may provide path visual stimulation according to a reference set based on personal information or personal identification information. For example, the stimulation providing device 111 may include a touch screen or a screen. The stimulation providing device 111 may provide path visual stimulation such that the target image of a specific coordinate is moved. The direction and location in which the target image moves may be set based on personal information or personal identification information. The stimulation providing device 111 may provide a visual stimulation path such as a curved shape, a straight shape, a spiral shape, a square shape, or a combination thereof. The shape of the path may be set based on personal information or personal identification information. The stimulation providing device 111 may provide path visual stimulation several times. The path visual stimulations are may be different each time.

In operation S530, the health data collection device 110 measures the tracking time and accuracy of the path. The user may trace the path using a touch pen or a laser pointer. The health data collection device 110 may sense the touch pen or the laser pointer of the user and measure the tracking time and accuracy of the path. Based on the tracing time of the path, the nerve response time may be calculated. The health data collection device 110 may measure the accuracy based on the ratio of the touch or laser reaching a certain radius around the target image to the target image. The health data collection device 110 may detect the deviation of the path of the touch pen or the laser pointer to calculate the error ratio and the accuracy ratio. Accuracy may be used as an index indicating the degree of hand tremor, cognitive power, and the like.

The health data collection device 110 may provide path visual stimulation several times and measure the response to the path tracing several times. The average and standard deviation of the path tracking times and accuracies measured the set number of times may be calculated. The reliability range may be set based on the average and the standard deviation. A path tracking time and an accuracy out of the reliability range among the measured response times and accuracies may be determined as errors and eliminated. That is, the reliability of response related information may be improved.

In operation S540, the bio signal measurement device 112 measures the bio signal. The response to path visual stimulation differs from the bio signal in that it is the intended behavioral pattern. The bio signal may be measured with the progress of operations S520 and S530. The bio signal measurement device 112 may measure the bio signal based on personal information or personal identification information. The bio signal measurement device 112 measures a first bio signal before providing path visual stimulation. The bio signal measurement device 112 measures a second bio signal while providing path visual stimulation. The bio signal measurement device 112 measures a third bio signal after providing path visual stimulation. For example, the bio signal may include at least one of bio signals on electrocardiogram, pulse wave, skin conductivity, skin temperature, and brain wave.

In operation S550, the controller 113 extracts a feature factor from the measured bio signal. For example, the controller 113 may extract feature factors for electrocardiogram, pulse wave, skin conductivity, skin temperature, and brain wave from the bio signal. In operation S560, the controller 113 generates physiological function data. The controller 113 may extract physiological functions for a feature factor responding to path visual stimulation to generate physiological function data. For example, the controller 113 may generate physiological function data related to a nerve response from a feature factor. The controller 113 may generate physiological function data on executive power. The executive power will be understood as a kind of cognitive ability that indicates the degree of executing a task when a specific stimulation or task is given.

In operation S570, the controller 113 processes the generated data. The generated data may include bio signal data obtained by converting the measured bio signal, stimulation data that includes information about electrical stimulation, feature factor data, and physiological function data. In addition, the generated data may additionally include information related to the path tracking time and accuracy generated in operation S530. The controller 113 classifies the generated data. The health data collection device 110 may transmit data generated using the communication device to the management server 120. The transmitted data is stored in the data storage unit 121 as visit data.

After the entire process is terminated, the management server 120 may analyze the stored visit data. When path visual stimulation is provided, the degree of disease or aging related to the nerve response speed may be analyzed. Due to aging, central nerve system actions, peripheral nerve system abnormalities, and nerve bundle abnormalities may occur. Therefore, the nerve response speed may be reduced. That is, the physiological function data related to nerve response speed may be used to analyze health functions such as dementia, brain disease, or aging.

In addition, when path visual stimulation is provided, variations in cognitive ability may occur. Physiological function data related to executive power may be generated using variations in cognitive ability. Due to dementia, brain disease, and the deterioration of physical and psychological health state, cognitive function and executive power may be lowered. The physiological function data related to executive power may be used to analyze health functions such as dementia, brain disease, or aging. The management server 120 may compare the previous visit data with the currently stored visit data to analyze the health variation of the user and predict the health state. Also, the management server 120 may generate personal identification information using the visit data.

Figure 17:
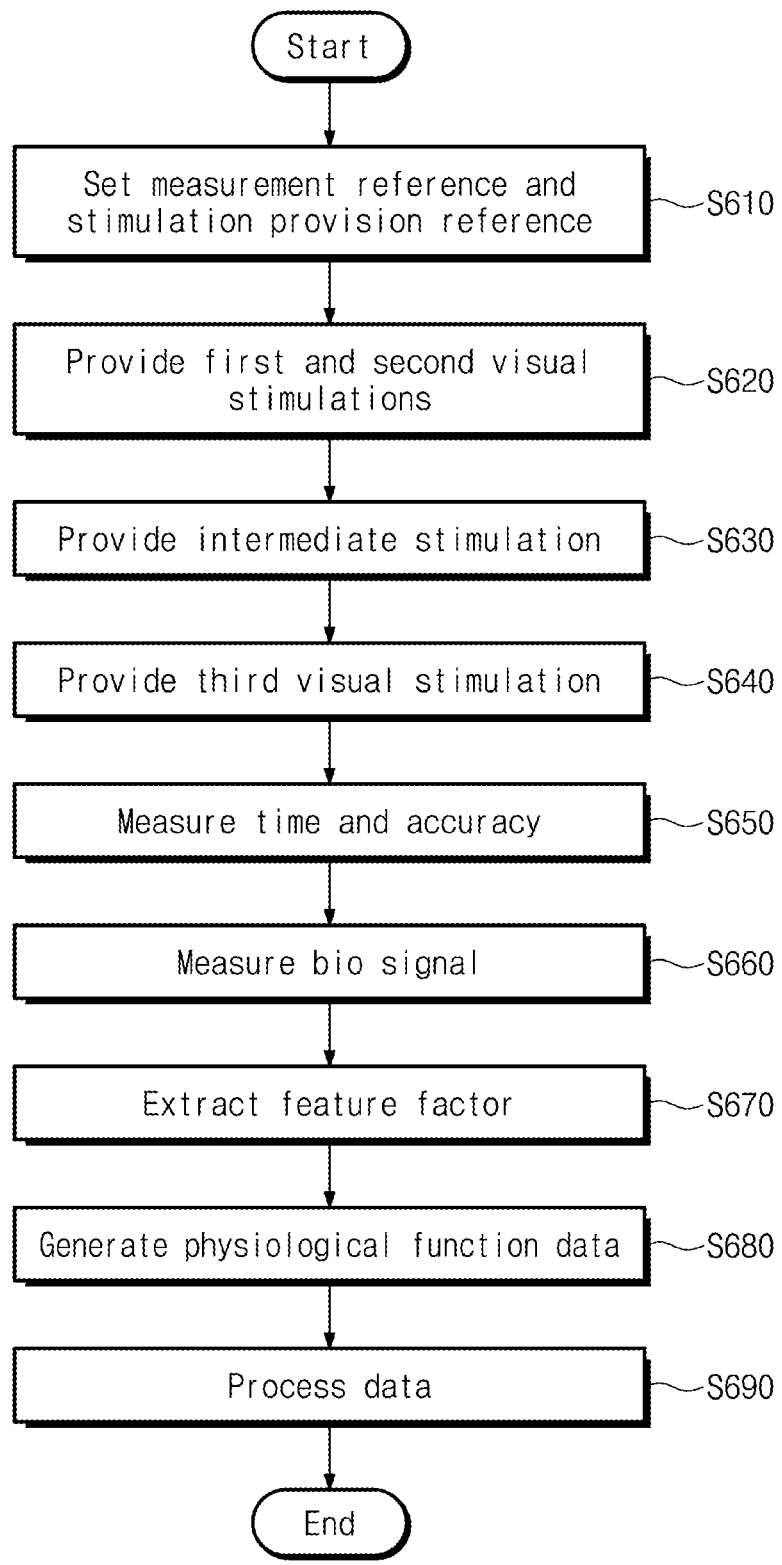
FIG. 17 is a view for explaining a process of collecting and processing physiological function data on memory.

FIG. 17 is a view for explaining a process of collecting and processing physiological function data on memory. The process of FIG. 17 will be understood as one embodiment, and methods for collecting and processing physiological function data on memory are not limited to FIG. 17. The process of FIG. 17 may be performed in the health evaluation system 100 of FIG. 1 or the health evaluation system 200 of FIG. 2. Also, some operations shown in FIG. 17 may be performed in any one of the health data collection devices 300 to 700 of FIGS. 3 to 7. Hereinafter, the process of FIG. 17 will be described in correspondence to the components of FIG. 1.

In operation S610, the health data collection device 110 sets a bio signal measurement reference and a reference for providing stimulation to the user. The health data collection device 110 sets the bio signal measurement reference and the reference for providing stimulation to the user based on personal information or personal identification information. The health data collection device 110 may determine the type of stimulation to be provided to the user, and the time point of providing stimulation based on the personal information or the personal identification information. In addition, the health data collection device 110 may determine the number of times of providing stimulation.

In operation S620, the stimulation providing device 111 provides the user with first and second visual stimulations. The shape of the displayed first and second visual stimulations and the time point of providing the first and second visual stimulations may be set based on personal information or personal identification information. The first and second visual stimulations may be provided to generate physiological function data related to short-term memory. The first and second visual stimulations may be provided sequentially. The first visual stimulation is provided and after a predetermined time, the second visual stimulation may be provided. At this time, the first visual stimulation may represent a memory target, and the second visual stimulation may be the stimulation that instructs the memory for the first visual stimulation.

In operation S630, the stimulation providing device 111 provides intermediate stimulation to a user. The intermediate stimulation may be stimulation for lowering the user's concentration on the first visual stimulation. The short-term memory is related to the ability to extract memory in a short time, and the long-term memory is related to the ability to extract memory that varies over time. The intermediate stimulation may be provided to distinguish short-term memory from long-term memory. The intermediate stimulation may be stimulation provided to generate physiological function data related to executive power, stress, or concentration.

In operation S640, the stimulation providing device 111 provides third visual stimulation to a user. The shape of the displayed third visual stimulation and the time point of providing the third visual stimulation may be set based on personal information or personal identification information. The third visual stimulation may be provided to generate physiological function data related to long-term memory. The third visual stimulation may be a stimulation that instructs the memory for the first visual stimulation.

During operations S620 to S640, other sensory stimulations such as olfactory, auditory, taste, or tactile stimulation may be provided in parallel or in series with the first to third visual stimulations. In other words, memory for other sensory stimulations may be further analyzed. In this case, memory for combinations of various sensory stimulations may be derived. Thus, sensitivity to various sensations may be analyzed.

In operation S650, the health data collection device 110 measures a response time and an accuracy. For example, when the second visual stimulation is provided, the user may provide memory information about the first visual stimulation to the health data collection device 110 in various ways. At this time, the response time related to short-term memory may be measured. When the third visual stimulation is provided, the user may provide memory on the first visual stimulation to the health data collection device 110 in various ways. At this time, the response time related to long-term memory may be measured. Also, the accuracy of the memory information provided by the user may be measured. The response time and accuracy may be measured when operations S620 and S640 are performed.

The health data collection device 110 may provide the first to third stimulations several times and measure the responses to it several times. The average and standard deviation of the response times and accuracies measured the set number of times may be calculated. The reliability range may be set based on the average and the standard deviation. A response time and an accuracy out of the reliability range among the measured response times and accuracies may be determined as errors and eliminated. That is, the reliability of response related information may be improved.

In operation S660, the bio signal measurement device 112 measures the bio signal. The providing of memory information in response to stimulation differs from the bio signal in that it is the intended behavioral pattern for the first to third visual stimulations. The bio signal may be measured with the progress of operations S620 to S640. The bio signal measurement device 112 may measure the bio signal based on personal information or personal identification information. The bio signal measurement device 112 measures a first bio signal before providing stimulation. The bio signal measurement device 112 measures a second bio signal while providing stimulation. The bio signal measurement device 112 measures a third bio signal after providing stimulation. Stimulation that provides a temporal reference of a bio signal measurement may include first to third stimulations, and intermediate stimulation.

In operation S670, the controller 113 extracts a feature factor from the measured bio signal. In operation S680, the controller 113 generates physiological function data. The controller 113 may extract physiological functions for a feature factor responding to the first to third visual stimulations to generate physiological function data. The controller 113 may generate physiological function data on memory from the feature factor.

In operation S690, the controller 113 processes the generated data. The generated data may include bio signal data obtained by converting the measured bio signal, stimulation data that includes information about electrical stimulation, feature factor data, and physiological function data. In addition, the generated data may additionally include data related to the response of the user, such as response time information and accuracy information generated in operation S650. The controller 113 classifies the generated data. The health data collection device 110 may transmit data generated using the communication device to the management server 120. The transmitted data is stored in the data storage unit 121 as visit data.

After the entire process is terminated, the management server 120 may analyze the stored visit data. When physiological function data on memory is collected, changes in the central nerve system or peripheral nerve system may be analyzed. The physiological function data related to memory may be used to analyze health functions such as dementia, brain disease, or aging. The management server 120 may compare the previous visit data with the currently stored visit data to analyze the health variation of the user and predict the health state. Also, the management server 120 may generate personal identification information using the visit data.

Figure 18:
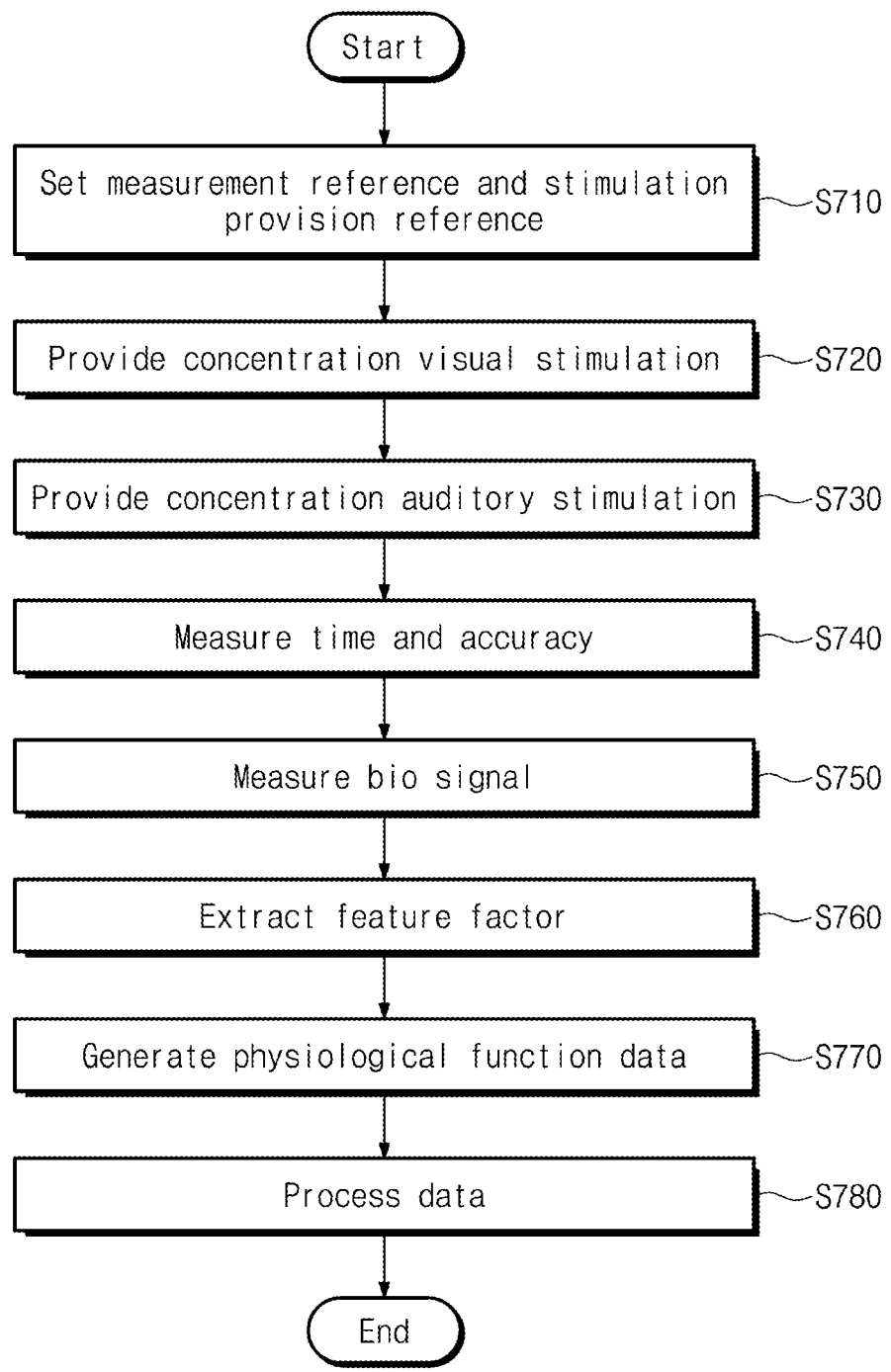
FIG. 18 is a view for explaining a process of collecting and processing physiological function data on concentration.

FIG. 18 is a view for explaining a process of collecting and processing physiological function data on concentration. The process of FIG. 18 will be understood as one embodiment, and methods for collecting and processing physiological function data on concentration are not limited to FIG. 18.

The process of FIG. 18 may be performed in the health evaluation system 100 of FIG. 1 or the health evaluation system 200 of FIG. 2. Also, some operations shown in FIG. 18 may be performed in any one of the health data collection devices 300 to 700 of FIGS. 3 to 7. Hereinafter, the process of FIG. 18 will be described in correspondence to the components of FIG. 1.

In operation S710, the health data collection device 110 sets a bio signal measurement reference and a reference for providing stimulation to the user. The health data collection device 110 sets the bio signal measurement reference and the reference for providing stimulation to the user based on personal information or personal identification information. The health data collection device 110 may determine the type of stimulation to be provided to the user, and the time point of providing stimulation based on the personal information or the personal identification information. In addition, the health data collection device 110 may determine the number of times of providing stimulation.

In operation S720, the stimulation providing device 111 provides concentration visual stimulation to a user. The concentration visual stimulation may include visual stimulation for concentration and visual stimulation for dispersing the concentration. The visual stimulation for concentration and the visual stimulation for dispersing concentration may be provided at the same time or at time intervals. The concentration visual stimulation may be set based on personal information or personal identification information.

In operation S730, the stimulation providing device 111 provides concentration auditory stimulation to a user. The concentration auditory stimulation may include auditory stimulation for concentration and auditory stimulation for dispersing the concentration. For example, auditory stimulation for concentration may be a voice for sentence or word. The auditory stimulation for dispersing concentration may be a voice for another sentence or word. The auditory stimulation for concentration and the auditory stimulation for dispersing concentration may be provided at the same time or at time intervals. The concentration auditory stimulation may be set based on personal information or personal identification information.

The stimulation providing device 111 may provide other sensory stimulations besides concentration visual stimulation or concentration auditory stimulation. For example, the stimulation providing device 111 may provide more concentration tactile stimulation. Also, unlike operations S720 and S730, stimulation for concentration and stimulation for dispersing concentration may be provided to a user with different sensory stimulations. For example, the stimulation for concentration may be visual stimulation, and the stimulation for dispersing concentration may be tactile stimulation.

In operation S740, the health data collection device 110 measures a response time and an accuracy. When the stimulation for dispersing concentration is provided, the user may provide concentration information corresponding to the stimulation for concentration to the health data collection device 110 in various ways. When the concentration information is provided to the health data collection device 110, the response time may be measured. Also, the accuracy of the concentration information provided by the user may be measured. For example, a specific word or sentence may be provided as visual stimulation for concentration, and a word or sentence with some difference may be provided as visual stimulation for dispersing concentration. The user may provide the health data collection device 110 with concentration information based on the difference between the visual stimulation for concentration and the visual stimulation for dispersing concentration. The response time is measured based on the reception time point of the concentration information, and the accuracy of the concentration information itself may be measured.

The health data collection device 110 may provide concentration visual stimulation and concentration auditory stimulation several times and measure the response thereto several times. The average and standard deviation of the response times and accuracies measured the set number of times may be calculated. The reliability range may be set based on the average and the standard deviation. A concentration time and an accuracy out of the reliability range among the measured response times and accuracies may be determined as errors and eliminated. That is, the reliability of response related information may be improved.

In operation S750, the bio signal measurement device 112 measures the bio signal. The providing of concentration information in response to stimulation differs from the bio signal in that it is the intended behavioral pattern for concentration visual stimulation or concentration auditory stimulation. The bio signal may be measured with the progress of operations S720 to S730. The bio signal measurement device 112 may measure the bio signal based on personal information or personal identification information. The bio signal measurement device 112 measures a first bio signal before providing concentration visual stimulation or concentration auditory stimulation. The bio signal measurement device 112 measures a second bio signal while providing concentration visual stimulation or concentration auditory stimulation. The bio signal measurement device 112 measures a third bio signal after providing concentration visual stimulation or concentration auditory stimulation.

In operation S760, the controller 113 extracts a feature factor from the measured bio signal. In operation S770, the controller 113 generates physiological function data. The controller 113 may extract physiological functions for a feature factor responding to concentration visual stimulation or concentration auditory stimulation to generate physiological function data. The controller 113 may generate physiological function data on concentration from the feature factor. In addition, the controller 113 may further generate physiological function data according to a concentration related nerve response. For example, the controller 113 may further generate physiological function data on stress that appears as the concentration changes.

In operation S780, the controller 113 processes the generated data. The generated data may include bio signal data obtained by converting the measured bio signal, stimulation data that includes information about electrical stimulation, feature factor data, and physiological function data. In addition, the generated data may additionally include data related to the response of the user, such as response time information and accuracy information generated in operation S740. The controller 113 classifies the generated data. The health data collection device 110 may transmit data generated using the communication device to the management server 120. The transmitted data is stored in the data storage unit 121 as visit data.

After the entire process is terminated, the management server 120 may analyze the stored visit data. When physiological function data on concentration is collected, changes in the central nerve system or peripheral nerve system may be analyzed. If complex concentration stimulations are provided, aging or damage to the brain region may be analyzed. The management server 120 may compare the previous visit data with the currently stored visit data to analyze the health variation of the user and predict the health state. Also, the management server 120 may generate personal identification information using the visit data.

FIG. 19 is a view for explaining a process of collecting and processing physiological function data on stress. The process of FIG. 19 will be understood as one embodiment, and methods for collecting and processing physiological function data on stress are not limited to FIG. 19. The process of FIG. 19 may be performed in the health evaluation system 100 of FIG. 1 or the health evaluation system 200 of FIG. 2. Also, some operations shown in FIG. 19 may be performed in any one of the health data collection devices 300 to 700 of FIGS. 3 to 7. Hereinafter, the process of FIG. 19 will be described in correspondence to the components of FIG. 1.

In operation S810, the health data collection device 110 sets a bio signal measurement reference and a reference for providing stimulation to the user. The health data collection device 110 sets the bio signal measurement reference and the reference for providing stimulation to the user based on personal information or personal identification information. The health data collection device 110 may determine the type of stimulation to be provided to the user, and the time point of providing stimulation based on the personal information or the personal identification information. In addition, the health data collection device 110 may determine the number of times of providing stimulation.

In operation S820, the stimulation providing device 111 provides stress to a user. For example, stress stimulation may be a visual stimulation in which an equation that requires calculation is displayed. However, the embodiment is not limited thereto, and the stress stimulation may be other sensory (e.g., auditory or tactile) stimulation or electrical stimulation. In addition, the stress stimulation may be a complex sensory stimulation.

In operation S830, the health data collection device 110 measures a response time and an accuracy. When the stress concentration is provided, the user may provide input information corresponding to the stress stimulation to the health data collection device 110 in various ways. For example, if the visual stimulation in which an equation is displayed is provided as stress stimulation, the input information may be information related to the result of a specific equation. When the input information is provided to the health data collection device 110, the response time may be measured. Also, the accuracy of the input information provided by the user may be measured.

The health data collection device 110 may provide stress stimulation several times and measure the response thereto several times. The average and standard deviation of the response times and accuracies measured the set number of times may be calculated. The reliability range may be set based on the average and the standard deviation. A concentration time and an accuracy out of the reliability range among the measured response times and accuracies may be determined as errors and eliminated. That is, the reliability of response related information may be improved.

In operation S840, the bio signal measurement device 112 measures the bio signal. The providing of input information in response to stimulation differs from the bio signal in that it is the intended behavioral pattern for stress stimulation. The bio signal may be measured with the progress of operation S820. The bio signal measurement device 112 may measure the bio signal based on personal information or personal identification information. The bio signal measurement device 112 measures a first bio signal before providing stress stimulation. The bio signal measurement device 112 measures a second bio signal while providing stress stimulation. The bio signal measurement device 112 measures a third bio signal after providing stress stimulation.

In operation S850, the controller 113 extracts a feature factor from the measured bio signal. In operation S860, the controller 113 generates physiological function data. The controller 113 may extract physiological functions for a feature factor responding to stress stimulation to generate physiological function data. The controller 113 may generate physiological function data on stress from the feature factor.

In operation S870, the controller 113 processes the generated data. The generated data may include bio signal data obtained by converting the measured bio signal, stimulation data that includes information about electrical stimulation, feature factor data, and physiological function data. In addition, the generated data may additionally include data related to the response of the user, such as response time information and accuracy information generated in operation S830. The controller 113 classifies the generated data. The health data collection device 110 may transmit data generated using the communication device to the management server 120. The transmitted data is stored in the data storage unit 121 as visit data.

After the entire process is terminated, the management server 120 may analyze the stored visit data. When physiological function data on stress is collected, variations in the central nerve system or peripheral nerve system may be analyzed. Changes in the homeostasis, aging, and nerve system of the human body may be analyzed based on variations in the analyzed central nerve system or peripheral nerve system. The management server 120 may compare the previous visit data with the currently stored visit data to analyze the health variation of the user and predict the health state. Also, the management server 120 may generate personal identification information using the visit data.

The health data collection device, the health evaluation method, and the health evaluation system according to an embodiment of the inventive concept may collect personalized health data using personal identification information.

According to an embodiment of the inventive concept, health data optimized for the evaluation of a health state may be collected by measuring bio signals in a stabilization state and a perturbation state.

According to an embodiment of the inventive concept, changes in health progression, possibility of disease occurrence, changes in disease progression, or aging progression may be evaluated and predicted.

An embodiment of the invention may be implemented as a computer implemented method or as a non-transitory computer readable medium with computer executable instructions stored thereon. In an embodiment, when executed by the processor, the computer readable instructions may perform a method according to at least one aspect of the invention.

Although the exemplary embodiments of the inventive concept have been described, it is understood that the inventive concept should not be limited to these exemplary embodiments but various changes and modifications can be made by one ordinary skilled in the art within the spirit and scope of the inventive concept as hereinafter claimed.

What is claimed is:

1. A health data collection device using biometric information corresponding to a plurality of signals occurred from a user, comprising:
   an input device configured to receive personal information of the user;

a stimulation providing device configured to provide a stimulation to allow the user in a stabilization state to be changed to a perturbation state, the stimulation providing device including a plurality of stimulation providers configured to provide different stimulations;

a bio signal measurement device including a plurality of sensors, each of the plurality of sensors configured to measure a first bio signal in the stabilization state for each of the different stimulations and measure a second bio signal in the perturbation state for said each of the different stimulations;

a controller configured to control the stimulation providing device and the bio signal measurement device based on the personal information when the user first uses the health data collection device and based on personal identification information after the first use of the health data collecting device, extract first and second feature factors from the first and second bio signals, respectively, classify the first and second feature factors according to a plurality of physiological functions, and generate physiological function data based on a change amount of the classified first and second feature factors; and a communication device configured to transmit data for the first and second bio signals, data for the first and second feature factors, and the physiological function data to a management server and receive the personal identification information from the management server, the personal identification information being generated and updated by analyzing a health variation of the user based on an accumulation of the physiological function data whenever the physiological function data is provided to the management server by each use of the health data collection device and patterning, as image data, a health trend of the user using the analyzed health variation, wherein each of the first and second bio signals comprises at least one of electrocardiogram, pulse wave, skin conductivity, and skin temperature.

2. The health data collection device of claim 1, wherein the input device receives the personal information including at least one of name, sex, age, and human body information of the user, and the human body information comprises height, weight, fingerprint, iris, and pulse information or disease information of the user.

3. The health data collection device of claim 1, wherein the controller controls at least one of an intensity of the stimulation, a type of the stimulation, and a time point of providing the stimulation based on the personal information or the personal identification information.

4. The health data collection device of claim 1, wherein the plurality of stimulation providers includes a first stimulation provider which provides an electrical stimulation to the user, wherein the plurality of sensors includes a first sensor which measures the first bio signal before providing the electrical stimulation and measures the second bio signal while providing the electrical stimulation.

5. The health data collection device of claim 1, wherein the plurality of stimulation providers includes a second stimulation provider which provides a pressure stimulation to the user, wherein the plurality of sensors includes a second sensor which measures the first bio signal before providing the pressure stimulation and measures the second bio signal while providing the pressure stimulation.

6. The health data collection device of claim 1, wherein the plurality of stimulation providers includes a third stimulation provider which provides the user with a sensory stimulation including at least one of visual, auditory, olfactory, tactile, and taste, wherein the plurality of sensors includes a third sensor which measures the first bio signal before providing the sensory stimulation and measures the second bio signal while providing the sensory stimulation.

7. The health data collection device of claim 6, wherein the third stimulation provider comprises a touch display for providing a visual stimulation to the user and recognizing a touch inputted by the user in response to the visual stimulation, and wherein the controller generates information on a response based on the recognized touch, and generates physiological function data on memory, executive power, concentration, and stress based on the first and second bio signals and the information on the response.

8. The health data collection device of claim 6, further comprising a laser detection sensor for detecting a laser light irradiated in response to the sensory stimulation, wherein the controller generates information on a response based on the detected laser light, and generates physiological function data on at least one of memory, executive power, concentration, and stress based on the first and second bio signals and the information on the response.

9. The health data collection device of claim 1, wherein the controller sets a bio signal measurement reference depending on the personal information or the personal identification information.

10. The health data collection device of claim 1, wherein said each of the plurality of sensors further measures a third bio signal in a restored stabilization state after the perturbation state for said each of the different stimulations, and wherein the controller generates the physiological function data based on the first to third bio signals.

11. The health data collection device of claim 10, wherein the controller generates the physiological function data based on at least one of a change amount of features factors extracted from the second bio signal and the third bio signal and a change amount of features factors extracted from the first bio signal and the third bio signal, and the change amount of the classified features factors extracted from the first bio signal and the second bio signal.

12. A health evaluation method using biometric information corresponding to a plurality of signals, comprising:

receiving, by a controller of a health data collection device, personal information from an input device of the health data collection device or personal identification information corresponding to a user from a management server;

setting, by the controller, a bio signal measurement reference for each of a plurality of bio signal measurement devices and a stimulation provision reference for each of a plurality of stimulation providing devices based on the personal information when the user first uses the health data collection device and based on the personal identification information after the first use of the health data collection device, the plurality of bio signal measurement devices and the plurality of stimulation providing devices being included in the health data collection device;

measuring, by said each of the plurality of bio signal measurement devices, a first bio signal from the user in a stabilization state according to the bio signal measurement reference;

providing, by said each of the plurality of stimulation providing devices, a stimulation to the user according to the stimulation provision reference;

measuring, by said each of the plurality of bio signal measurement devices, a second bio signal from the user in a perturbation state according to the bio signal measurement reference;

generating, by the controller, physiological function data based on the first bio signal and the second bio signal;

providing, by a communication device of the health data collection device, the physiological function data to the management server; and generating and updating, by the management server, the personal identification information by analyzing a health variation of the user based on an accumulation of the physiological function data whenever the physiological function data is provided to the management server by each use of the health data collection device and patterning, as image data, a health trend of the user using the analyzed health variation, wherein the generating of the physiological function data comprises:

extracting, by the controller, first feature factors from the first bio signal and second feature factors from the second bio signal;

classifying the first and second feature factors according to a plurality of physiological functions; and generating, by the controller, the physiological function data based on a change amount of the classified first feature factors and the classified second feature factors, and wherein each of the first and second bio signals comprises at least one of electrocardiogram, pulse wave, skin conductivity, and skin temperature.

13. The method of claim 12, further comprising:

providing, by the communication device, bio signal data generated by converting the first and second bio signals, stimulation data, and feature factor data generated by converting the first and second feature factors to the management server;

classifying, by the management server, the physiological function data to generate health function data; and grouping, by the management server, the bio signal data, the stimulation data, the feature factor data, the physiological function data, and the health function data as visit data, and storing the visit data.

14. The method of claim 13, further comprising comparing, by the management server, the visit data and previously-stored visit data to analyze the health variation and predict a health function.

15. The method of claim 13, further comprising comparing, by the management server, the visit data and previously stored visit data to generate the personal identification information.

16. The method of claim 13, further comprising measuring, by each of the plurality of bio signal measurement devices, a third bio signal from the user according to the bio signal measurement reference after the providing of the stimulation is terminated, wherein the extracting the physiological function data comprises comparing the first to third bio signals to extract the physiological function data.

17. A health evaluation system using biometric information corresponding to a plurality of signals, comprising:

a health data collection device configured to set a bio signal measurement reference and a stimulation provision reference based on personal information of a user when the user first uses the health data collection device and based on personal identification information after the first use of the health data collection device, provide a stimulation to the user according to the stimulation provision reference, measure a first bio signal for each of the plurality of signals occurred from the user before providing the stimulation according to the bio signal measurement reference, measure a second bio signal for each of the plurality of signals occurred from the user while providing the stimulation according to the bio signal measurement reference, extract first and second feature factors from the first and second bio signals, respectively, according to a reference set based on the personal information or the personal identification information, classify the first and second feature factors according to a plurality of physiological functions, generate physiological function data based on a change amount of the classified first feature factors and the classified second feature factors, and transmit the physiological function data to a management server; and the management server configured to receive the physiological function data, analyze a health variation of the user based on an accumulation of the received physiological function data whenever the physiological function data is provided to the management server by each use of the health data collection device, and generate and update the personal identification information by patterning, as image data, a health trend of the user using the analyzed health variation, wherein each of the first and second bio signals comprises at least one of electrocardiogram, pulse wave, skin conductivity, and skin temperature.

18. The health evaluation system of claim 17, wherein the health data collection device comprises:

a plurality of stimulation providing devices configured to provide different stimulations to the user;

a plurality of bio signal measurement devices configured to measure the first bio signal and the second bio signal for each of the different stimulations; and a controller configured to set the reference for extracting the first and second feature factors based on the personal information or the personal identification information to extract the first and second feature factors and generate the physiological function data based on the first and second feature factors.

19. The health evaluation system of claim 17, wherein the management server comprises:

a data storage unit configured to store the physiological function data by each use of the health data collection device; and a health function analysis device configured to compare the physiological function data with previously-stored physiological function data to generate health variation analysis data and the personal identification information.

* * * * *